(12) United States Patent
Dinesh Kumar et al.

(10) Patent No.: US 10,208,353 B2
(45) Date of Patent: Feb. 19, 2019

(54) BIOMARKERS USEFUL FOR DETECTION OF TYPES, GRADES AND STAGES OF HUMAN BREAST CANCER

(71) Applicant: Council of Scientific and Industrial Research, New Delhi (IN)

(72) Inventors: Lekha Dinesh Kumar, Hyderabad (IN); Vinod Kumar Verma, Hyderabad (IN); Rekha A. Nair, Trivandrum (IN); Jem Prabhakar, Trivandrum (IN); Jayasree Kattoor, Trivandrum (IN)

(73) Assignee: Council of Scientific and Industrial Research, New Delhi (IN)

( * ) Notice: Subject to any disclaimer, the term of this patent is extended or adjusted under 35 U.S.C. 154(b) by 121 days.

(21) Appl. No.: 14/352,804

(22) PCT Filed: Oct. 17, 2012

(86) PCT No.: PCT/IB2012/002090
§ 371 (c)(1),
(2) Date: Apr. 18, 2014

(87) PCT Pub. No.: WO2013/057567
PCT Pub. Date: Apr. 25, 2013

(65) Prior Publication Data
US 2015/0080244 A1 Mar. 19, 2015

(30) Foreign Application Priority Data
Oct. 19, 2011 (IN) .......................... 1142/DEL/2011

(51) Int. Cl.
*C12Q 1/6886* (2018.01)
(52) U.S. Cl.
CPC ...... *C12Q 1/6886* (2013.01); *C12Q 2600/112* (2013.01); *C12Q 2600/158* (2013.01); *C12Q 2600/16* (2013.01); *C12Q 2600/178* (2013.01)
(58) Field of Classification Search
None
See application file for complete search history.

(56) References Cited

U.S. PATENT DOCUMENTS

| | | | |
|---|---|---|---|
| 2004/0191783 A1* | 9/2004 | Leclercq | C12Q 1/6837 506/16 |
| 2010/0173288 A1* | 7/2010 | Zhang et al. | 435/6 |
| 2010/0179213 A1* | 7/2010 | Patrawala | C12N 15/113 514/44 R |
| 2010/0286234 A1 | 11/2010 | Elmen et al. | |
| 2012/0088687 A1* | 4/2012 | Goel | C12Q 1/6886 506/9 |

FOREIGN PATENT DOCUMENTS

| | | |
|---|---|---|
| EP | 2638912 A1 | 9/2013 |
| WO | WO-2007/016548 | 2/2007 |
| WO | WO-2010/139810 A1 | 12/2010 |
| WO | WO-2013/057567 | 4/2013 |

OTHER PUBLICATIONS

Kozomara et al. (Nucleic Acids Research published online Oct. 30, 2010 vol. 39 p. D152-D157).*
Cobb et al (Crit Care Med 2002 vol. 30 p. 2711) (Year: 2002).*
"International Application No. PCT/IB2012/002090, International Search Report dated Apr. 9, 2013", (Apr. 9, 2013), 8 pgs.
Blenkiron, C., et al., "MicroRNA expression profiling of human breast cancer identifies new markers of tumor subtype", Genome Biol., 8(10), (2007), R214.
Cochrane, D. R, et al., "MicroRNAs link estrogen receptor alpha status and Dicer levels in breast cancer", Horm Cancer, 1(6), (Dec. 2010), 306-19.
Lowery, A. J, et al., "MicroRNA signatures predict oestrogen receptor, progesterone receptor and HER2/neu receptor status in breast cancer.", Breast Cancer Res., 11(3), (2009), R27.
Wang, F., et al., "Correlation and quantitation of microRNA aberrant expression in tissues and sera from patients with breast tumor", Gynecol Oncol., 119(3), (Dec. 2010), 586-93.
Adams, Brian D., et al., "The Micro-Robonucleic Acid (miRNA) miR-206 Targets the Human Estrogen Receptorα (ERα) and Represses ERαMessenger RNA and Protein Expression in Breast Cancer Cell Lines". *Molecular Endocrinology* 21(5), (May 2007), 1132-1147.
Brennecke, Julius, et al., "bantam Encodes a Developmentally Regulated microRNA that Controls Cell Proliferation and Regulates the Proapoptotic Gene hid in *Drosophila*", Cell, vol. 113, (2003), 25-36.
Calin, George A., et al., "MicroRNA profiling reveals distinct signatures in B cell chronic lymphocytic leukemias", Proc. Natl. Acad. Sci. USA, 101(32), (2004), 11755-11760.
Calin, George A., et al., "MicroRNA signatures in human cancers", Nature Reviews Cancer, vol. 6, (Nov. 2006), 857-866.
Iorio, Marilena V., "MicroRNA Gene Expression Deregulation in Human Breast Cancer", Cancer Res., 65(16), (2005), 7065-7070.

(Continued)

*Primary Examiner* — Katherine D Salmon
(74) *Attorney, Agent, or Firm* — Schwegman Lundberg & Woessner, P.A.

(57) ABSTRACT

The present invention relates to biomarkers useful for detection of types, grades and stages of human breast cancer. The present invention particularly relates to the development of these identified biomarkers as a miRNA chip for the early and accurate diagnosis of human breast cancer. This patent application highlights the novelty in the utility of these miRNAs, that they could be used as a diagnostic kit (miRNA chip) for early and accurate detection of breast cancer grades, stages and subtypes. Few to hundreds of samples can be checked within a span of 2 to 3 hrs and hence this becomes an easy, fast, robust and high throughput technology for screening program for early detection of breast cancer.

Figure 5:
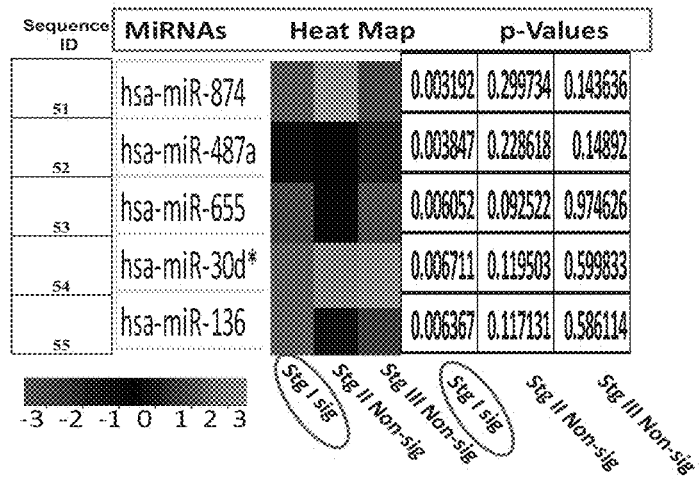

7 Claims, 5 Drawing Sheets
Specification includes a Sequence Listing.

(56) References Cited

OTHER PUBLICATIONS

Kong, William et al., "MicroRNA-155 Is Regulated by the Transforming Growth Factor β/Smad Pathway and Contributes to Epithelial Cell Plasticity by Targeting RhoA", *Molecular and Cellular Biology*, 28(22), (Nov. 2008), 6773-6784.

Lee, Rosalind C., et al., "The C. elegans Heterochronic Gene lin-4 Encodes Small RNAs with Antisense Complementarity to lin-14"*Cell*, 75, (1993) 843-854.

Lu, Jun, et al., "MicroRNA expression profiles classify human cancers", *Nature*, vol. 435, (2005), 834-838.

Ma, Linke, et al., "Tumour invasion and metastasis initiated by microRNA-10b in breast cancer", *Nature*, vol. 449, (2007), 682-688.

Mattie, Michael D., et al., "Optimized high-throughput microRNA expression profiling provides novel biomarker assessment of clinical prostate and breast cancer biopsies", *Molecular Cancer*, 5:24, (2006), 14 pgs.

Radojicic, Jelena, et al., "MicroRNA expression analysis in triple-negative (ER, PR and Her2/neu) breast cancer", *Cell Cycle* 10:3, (2011), 507-517.

Scott, Gary K., et al., "Coordinate Suppression of ERBB2 and ERBB3 by Enforced Expression of Micro-RNA miR-125α or miR-125b", *The Journal of Biological Chemistry*, 282(2), (2007), 1479-1486.

Thiery, Jean P., et al., "Epithelial-Mesenchymal Transitions in Development and Disease", *Cell*, 139, (2009), 871-890.

Yu, Fengyan, et al., "let-7 Regulates Self Renewal and Tumorigenicity of Breast Cancer Cells", *Cells*, 131, (2007), 1109-1123.

Yu, Zuoren, et al., "A cyclin D1/microRNA 17/20 regulatory feedback loop in control of breast cancer cell proliferation", *J. Cell Biol.*, 182(3), (2008), 509-517.

Zhu, Shuomin, et al., "MicroRNA-21 Targets the Tumor Suppressor Gene Tropomysin 1 (TPM1)", *The Journal of Biological Chemistry*, 282(19), (2007), 14328-14336.

"British Application Serial No. GB1408696.1, Examination Report dated Apr. 1, 2016", 4 pgs.

"British Application Serial No. GB1408696.1, Examination Report dated Jun. 2, 2014", 1 pg.

"British Application Serial No. GB1408696.1, Examination Report dated Oct. 23, 2015", 4 pgs.

"British Application Serial No. GB1408696.1, Response filed Feb. 23, 2016 to Examination Report dated Oct. 23, 2015", 7 pgs.

"British Application Serial No. GB1408696.1, Response filed Dec. 2, 2014 to Examination Report dated Jun. 2, 2014", 7 pgs.

"International Application No. PCT/IB2012/002090, International Preliminary Report on Patentability dated May 1, 2014", 12 pgs.

"International Application No. PCT/IB2012/002090, Written Opinion dated Apr. 9, 2013", 10 pgs.

De Souza Rocha Simonini, Pedro, et al., "Epigenetically Deregulated microRNA-375 Is Involved in a Positive Feedback Loop with Estrogen Receptor α in Breast Cancer Cells", Cancer Research, 70(22), (2010), 9175-9184.

Rothé, Françoise, et al., "Global MicroRNA Expression Profiling Identifies MiR-210 Associated with Tumor Proliferation, Invasion and Poor Clinical Outcome in Breast Cancer", PLoS One, 6(6), e20980, (Jun. 2011), 1-13.

\* cited by examiner

MicroRNAs significant in ER+ve breast cancers and non-significant in ER-ve breast cancers

Fig 1

| Sequence ID | MiRNAs | Heat Map | p-Values | |
|---|---|---|---|---|
| 1 | hsa-miR-623 | | 5.45E-07 | 0.123401 |
| 2 | hsa-miR-302d | | 6.69E-07 | 0.721909 |
| 3 | hsa-miR-562 | | 2.52E-07 | 0.876375 |
| 4 | hsa-miR-224 | | 3.11E-08 | 0.74462 |
| 5 | hsa-miR-452 | | 2.50E-09 | 0.12323 |
| 6 | hsa-miR-522 | | 1.10E-05 | 0.120844 |
| 7 | hsa-miR-124 | | 0.002761 | 0.982602 |
| 8 | hsa-miR-516a-5 | | 0.003282 | 0.781803 |
| 9 | hsa-miR-521 | | 0.001108 | 0.782736 |
| 10 | hsa-miR-627 | | 0.000596 | 0.81081 |
| 11 | hsa-miR-650 | | 0.000561 | 0.856289 |
| 12 | hsa-miR-205 | | 0.013754 | 0.744124 |
| 13 | hsa-miR-605 | | 0.003643 | 0.668146 |
| 14 | hsa-miR-375 | | 4.36E-06 | 0.269818 |
| 15 | hsa-miR-190b | | 2.40E-14 | 0.169269 |

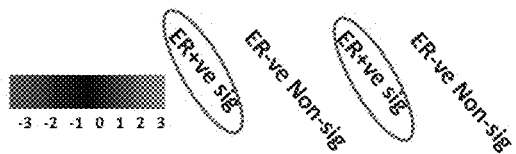

MicroRNAs significant in ER+ve breast cancers and non-significant in ER-ve breast cancers

Fig 2

| Sequence ID | MiRNAs | Heat Map | p-Values | |
|---|---|---|---|---|
| 16 | hsa-miR-887 | | 0.00958 | 0.298916 |
| 17 | hsa-miR-126* | | 0.003604 | 0.316368 |
| 18 | hsa-miR-188-5p | | 0.005266 | 0.869546 |
| 19 | hsa-miR-210 | | 0.006572 | 0.196152 |
| 20 | hsa-miR-20a | | 0.012503 | 0.79169 |
| 21 | hsa-miR-31 | | 0.005253 | 0.597875 |
| 22 | hsa-miR-187 | | 0.007196 | 0.114172 |
| 23 | hsa-miR-301b | | 0.003196 | 0.403403 |
| 24 | hsa-miR-142-3p | | 0.00151 | 0.142769 |
| 25 | hsa-miR-18a | | 0.003174 | 0.894561 |
| 26 | hsa-miR-137 | | 0.003334 | 0.542511 |
| 27 | hsa-miR-9 | | 0.000981 | 0.860445 |
| 28 | hsa-miR-135b* | | 0.011001 | 0.075302 |
| 29 | hsa-miR-934 | | 0.001526 | 0.200681 |

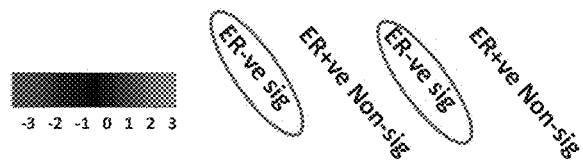

MicroRNAs significant in grade 2 and non-significant in grade 3 breast cancers
Fig 3
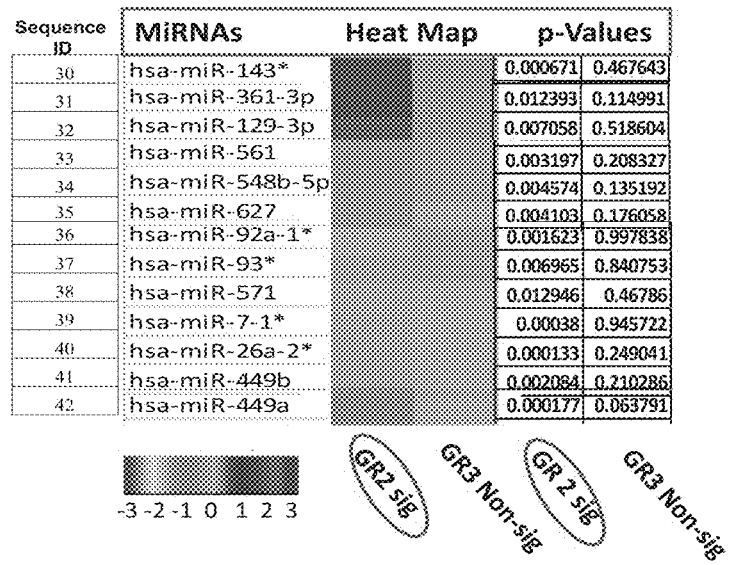
MicroRNAs significant in grade 3 and non-significant in grade 2 breast cancers
Fig 4
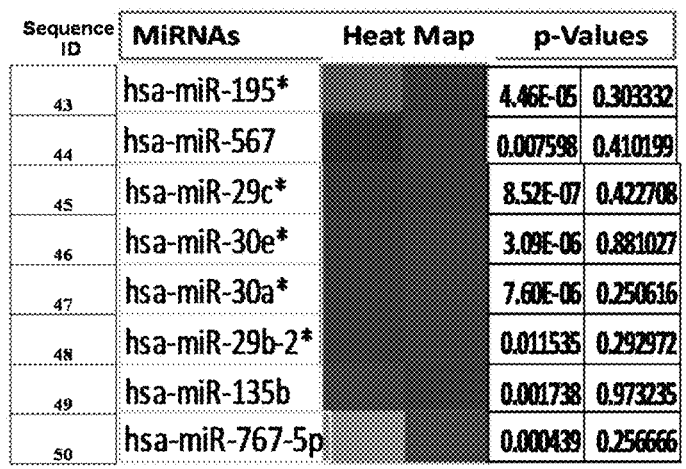

MicroRNAs significant in stage I and non-significant in stage II and III of grade 2 breast cancers MicroRNAs significant in stage II and non-significant in stage I and III of grade 2 breast cancers MicroRNAs significant in stage III and non-significant in stage I and II of grade 2 breast cancers MicroRNAs significant in stage I and non-significant in stage II and III of grade 3 breast cancers MicroRNAs significant in stage II and non-significant in stage I and III of grade 3 breast cancers MicroRNAs significant in stage III and non-significant in stage I and II of grade 3 breast cancers

BIOMARKERS USEFUL FOR DETECTION OF TYPES, GRADES AND STAGES OF HUMAN BREAST CANCER

PRIORITY CLAIM TO RELATED APPLICATIONS

This application is a U.S. national stage application filed under 35 U.S.C. § 371 from International Application Serial No. PCT/IB2012/002090, which was filed Oct. 17, 2012, and published as WO 2013/057567 on Apr. 25, 2013, and which claims priority to India Application No. 1142/DEL/2011, filed Oct. 19, 2011, which applications and publication are incorporated by reference as if reproduced herein and made a part hereof in their entirety, and the benefit of priority of each of which is claimed herein.

FIELD OF THE INVENTION

The present invention relates to a panel of biomarkers useful for detection of types, grades and stages of human breast cancer. The present invention particularly relates to the development of these identified biomarkers as a miRNA chip for the early and accurate diagnosis of human breast cancer. This patent application highlights the novelty in the utility of these miRNAs, that they could be used as a diagnostic kit (miRNA chip) for early and accurate detection of breast cancer grades, stages and subtypes.

BACKGROUND OF THE INVENTION AND DESCRIPTION OF PRIOR ART

Breast cancer is the leading cause of cancer-related deaths for women in the world. It is the second most common cancer in females in India and the early detection and treatment improve prognosis and survival rate, motivating the need for finding out novel non-invasive methods for early diagnosis of this disease. Presently, biopsy is the only method which confirms the diagnosis and different grades of cancer. Being an invasive method, it is time consuming and often uncomfortable for the patient. Moreover, the negative biopsy rate is significantly high, especially in screen detected and non palpable cancers suggesting that better molecular diagnostic techniques are needed to replace or compliment current biopsy techniques. Tissue characterization by pathologists for ER, PR and HER 2/Neu status and axillary lymph node status are the most important prognostic factors and 90% of those patients without nodal involvement have no further breast cancers detected in their lifetime. Presently, there is no established non-invasive test for confirming the axillary node status. Axillary nodal status is of major importance from a therapeutic and prognostic point of view. Moreover, majority of patients end up doing chemotherapy due to lack of reliable markers. Chemotherapeutic drugs currently used are also not specific to breast cancer. Therefore it is imperative to find novel biomarkers for early and accurate diagnosis and prognosis in breast cancer sparing the majority of patients from undergoing an axillary dissection. Such molecular signatures can also lead to good prognosis and help develop novel targeted treatments. Moreover, such an approach can accurately identify subgroups of patients who will really benefit from cytotoxic chemotherapy with its debilitating side effects.

The diagnosis of breast tumor starts with the screening techniques to confirm whether a lump is present or not. The noninvasive examination techniques existing are mammography, ultrasound or MR imaging which determine the presence of any tumors and also detect tumor size, invasion etc. To further confirm the tumor diagnosis and grading, Fine Needle Aspiration and Cytology (FNAC), core biopsy and excisional biopsy is required. Additional testing may include genetic screening that test for the status of hormones like ER, PR, and genes like HER2/neu etc. Chemotherapy is currently used for all cases of Infiltrating duct carcinomas of breast.

Mammography and ultrasound may identify a potential area of concern. MRI imaging requires injection of a dye, the side effects of which are not yet proven. Fine Needle Aspiration Cytology (FNAC) is not always as reliable as surgical biopsies in producing a conclusive diagnosis. Immunohistochemical analysis of ER, PR, HER2/neu, BRCA and PTEN requires lot of time to arrive at any final conclusion of disease progression. The available diagnostic methods present in the market are not up to the expectation that one can diagnose the early stages of disease and therapeutic measures can be optimized to completely prevent and cure the tumor at right time. These above mentioned imaging tools are not sensitive methods to detect early molecular changes occurring in the cell during initiation of the cancer. Tissue embedding, sectioning, staining are all cumbersome procedures and time consuming. Moreover, staging could be determined only after getting the final histopathology report and extensive metastatic workup. No existing technologies are there for more accurate staging of the disease for identifying suitable patient sub groups to tailor systemic treatment. *There are no proper fast and accurate molecular diagnostic tool for pathologists till now for accurate staging and grading. As far as current chemotherapy regimens are concerned, no targeted therapy is currently used.

Biomarkers constitute the most important field in cancer diagnosis. Cancer biomarkers are especially useful for early detection or diagnosis of the disease. Biomarkers can be used to screen patients, for classifying the different stages or grades of cancers and to predict prognosis and resistance to therapy. A tumour marker can be produced by tumour itself or by the body as a result of the disease. These biomolecules are quite often produced in abnormally large numbers in the cancerous tissues and often secreted to body fluids like blood, serum, urine etc. To identify molecular changes setting-in much before the disease initiation and progression, development of molecular biomarkers is extremely important.

MicroRNAs are small RNAs of 22-25 nucleotides in length with a major role in gene regulation. Since they are highly conserved between the genomes of related species and show a characteristic evolutionary divergence, computational analysis of miRNAs would augment the experimental analysis to identify those which are involved in the regulation of common genes and pathways leading to the development of cancer. Recently, oncomiRs, special classes of non-coding microRNAs are found to be associated with a large number of cancers. Consequently impaired miRNA expression is implicated in various tumours. This class of novel non-coding RNAs or microRNAs is expected to eventually identify previously unappreciated tumour suppressors and oncogenes and also address many questions about the origin, development and progression of breast cancer. Many studies have shown a deregulation with respect to the expression of these small RNAs in many tumours. It is imperative to know the expression profile of these microRNAs which would help us to classify, and associate these miRNAs with different stages and grades of tumours so as to develop them as novel biomarkers of various cancers. Thus the expression profiles could be used for classification, prognosis and diagnosis of human malignancies Present National and International Knowledge on the Utility of this Invention:

| S. No. | Name of the Inventor | objectives of investigation | Disease in which investigation is done | Name of biomarkers |
|---|---|---|---|---|
| 1. | Eugene M. S. (U.A.E.) | Detection of in vivo cell death | Infectious disease | Tissue specific miRNA |
| 2 | Talyor D. D. (U.S.A.) | Diagnostic marker | Diagnosis of cancer | Exosome associated miRNA |
| 3. | Chen, Jian-Wei (Taiwan) | Post treatment survival in cancer | Cancer | hsa-miR-137, hsa-miR-372, hsa-miR-182*, hsa-miR-221, and hsa-let-7a |
| 4. | Fischer T. J. (U.S.A.) | Early stage Breast cancer prognosis | Breast Cancer | Biomarkers of the invention are proteins |
| 5. | Dmitrovsky, E. (Hanover, NH, US) | miRNA as biomarker of human breast cancer | Breast cancer | MiRNAs are downregulated: hsa-miR-451, hsa-miR-143 and hsa-miR-145. |
| 6. | Croce C. M. (Columbus, OH, US) | Diagnosis, prognosis and treatment of breast cancer | Breast cancer | miRNAs are upregulated: hsa-miR-141, hsa-miR-200b, hsa-miR-200c, hsa-miR-221, hsa-miR-222 and hsa-miR-21. miRNAs are Down regulated: hsa-miR-125b-1, has-miR125b-2, has-miR-145, hsa -miR-21, has-miR-155, hsa -miR-10b |

Other Examples of Similar Studies:

OncomiRs are a special class of non-coding microRNAs found to be associated with a large number of cancers. Consequently impaired miRNA expression is implicated in various tumours. Various in vitro and in vivo studies have implicated an active role of microRNAs in breast cancer. Many reports on microRNAs indicated their role in cell proliferation and apoptosis growth and migration (1 & 2) suggesting that deregulation of these microRNA could lead to proliferative diseases like cancer. Also studies have shown that microRNA cluster mapped to the hotspot areas of the genome that are prone for cancer mutations (3 & 4). Their expression patterns show a general trend of down regulation in human cancer samples (5) indicating that most of them function as tumour suppressors. Though many profiling studies have revealed a different signature of the cancer samples compared to normal tissues, very few studies have been conducted which elucidates the functional role of each of these microRNAs. In breast cancer, microRNA miR 206 was found to inhibit the function of estrogen receptor gene ESR1. Later, it was found to be targeted by a set of microRNAs like miR 18a, miR 18b, miR 193b and miR 302c (6 & 7). CyclinD1 which is over expressed in majority of the cancers was identified as a direct target of miR 17-5p (8). Under expression status of miR 125a & b in HER 2 positive tumours indicated their role as a tumour suppressor of this gene. Analysis of triple negative (ER, PR and HER2/Neu) breast cancer patients showed that expression levels of miR 210, miR 21, and miR 221 play a significant role in the primary breast cancer vs normal samples (15). Down regulation of miR 200 family members in highly metastatic tumours and their up regulation in mesenchymal cells which initiated mesenchymal to epithelial transition depicted its role in metastasis (10). Let 7, one of the founder members of microRNAs are usually under expressed in tumours. One of the studies revealed that their down regulation induced BTI-Cs (Breast—Tumour initiating Cells) for tumour initiation, progression and metastasis and vice versa (11). MicroRNAs miR 21, miR 155 and miR 10b have been shown to play a role in tumour metastasis by targeting anti metastatic genes (12, 13,14). MiR-21 is over expressed in both male and female breast tumors compared with normal breast tissue and has been associated with advanced stage, lymph node positivity, and reduced survival time. Furthermore, existence of microRNAs either floating or in exosomes in the systemic circulation, has led to the possibility that such molecules may serve as biomarkers for early detection of cancers. Thus microRNA profiling is emerging as a powerful tool for diagnosis of breast cancer types, grades and stages. Although additional investigations are necessary to fully exploit the therapeutic use of miRNAs in breast cancer, there is increasing evidence that miRNAs have potential not only to facilitate the determination of diagnosis and prognosis and the prediction of response to treatment, but also to act as therapeutic targets and replacement therapies.

The drawback of these studies is that none of them was carried out in the specified stages of grades or subtypes of human breast cancer samples. Hence identifying the exact grade and stage of Breast Cancer is a boon for treatment of such kind of diseases.

OBJECTIVES OF THE INVENTION

The main objective of the present invention relates to biomarkers for diagnosis of different types, grades and stages of human breast cancer.

Another objective of the present invention relates to molecular biomarkers as indicators of cellular changes during the initiation and development of breast cancer.

Yet another objective of the present invention relates to a chip useful for detection and diagnosis of breast cancer.

Still another objective of the present invention is to provide a cheaper, accurate, robust and high throughput diagnostic kit for accurate diagnosis of human breast cancer.

SUMMARY OF THE INVENTION

Accordingly, the present invention relates to a panel of Biomarkers useful for screening and detection for the type, grade and stage of Breast cancer wherein the panel comprises of miRNA having sequence selected from the group consisting of Seq Id No. 1-107.

In an embodiment of the present invention a panel of Biomarkers useful for screening and detection for the type, grade and stage of Breast cancer wherein the panel comprises of miRNA having sequence selected from the group consisting of Seq Id No. 1-107

In an embodiment of the present invention the panel of Biomarkers wherein down regulation of microRNAs with Seq ID No. 1 to 12 and up regulation of Seq ID No. 13 to 15 detects ER+ve type of breast cancer.

In an embodiment of the present invention the panel of Biomarkers wherein down regulation of Seq. ID no. 16 & 17 and up regulation of Seq. ID no. 18 to 29 detects ER−Ve type of breast cancer.

In an embodiment of the present invention the panel of Biomarkers wherein down regulation of Seq. ID no. 30 to 36 and up regulation of Seq. ID no. 37 to 42 detects grade 2 breast cancer.

In an embodiment of the present invention the panel of Biomarkers wherein down regulation of Seq. ID no. 43 to 48 and up regulation of Seq. ID no. 49 & 50 detects grade 3 breast cancer.

In an embodiment of the present invention the panel of Biomarkers wherein down regulation of Seq. ID no. 51 to 55 detects stage I of grade 2 breast cancer.

In an embodiment of the present invention the panel of Biomarkers wherein down regulation of Seq. ID no. 56 to 73 detects stage II of grade 2 breast cancer.

In an embodiment of the present invention the panel of Biomarkers wherein down regulation of Seq. ID no. 74 & 75 and up regulation of Seq. ID no. 76 to 81 detects stage III of grade 2 breast cancer.

In an embodiment of the present invention the panel of Biomarkers wherein down regulation of Seq. ID no. 82 to 95 and up regulation of Seq. ID no. 96 & 97 detects stage I of grade 3 breast cancer.

In an embodiment of the present invention the panel of Biomarkers wherein down regulation of Seq. ID no. 98 to 100 and up regulation of Seq. ID no. 101 to 103 detects stage II of grade 3 breast cancer.

In an embodiment of the present invention the panel of Biomarkers wherein down regulation of Seq. ID no. 104 & 105 and upregulation of Seq. ID no. 106 & 107 detects stage III of grade 3 breast cancer.

In an embodiment of the present invention the panel of Biomarkers wherein the antisense sequences of the upregulated & downregulated microRNAs is of therapeutic use.

In yet another embodiment of the present invention an in vitro non-invasive method using the panel of biomarkers as claimed in claim 1 for detecting the type, grade and stage of breast cancer in a human subject.

In yet another embodiment of the present invention a panel of miRNA in the form of a DNA/RNA chip.

In yet another embodiment of the present invention a kit for detecting type, grade and stage of breast cancer wherein the kit consisting of:

Suitable reagents capable of detecting singly or a combination of the miRNA; Instruction manual for using the kit.

In yet another embodiment of the present invention use of the biomarkers and their antisense sequence for screening, diagnosis, prognosis and for preparing biological drugs for Breast Cancer.

In yet another embodiment of the present invention use of the biomarkers for detection of type, grades and stages of Breast Cancer.

In yet another embodiment of the present invention use of the biomarkers in diagnosis and prognosis of Breast cancer.

In yet another embodiment of the present invention use of the kit for detection of type, grades and stages of Breast Cancer.

BRIEF DESCRIPTION OF TABLES AND FIGURES

Table 1: The sequence IDs 1 to 15 lists the microRNAs which are significantly up/down regulated in ER+ve human breast cancer samples. The microRNA names along with their sequences and accession IDs are also described here. The exact fold change with which each microRNA is down regulated (indicated by +ve sign) and those which are up regulated 9 indicated by −Ve sign) are also given.

Table 2: The sequence IDs 16 to 29 lists the microRNAs which are significantly up/down regulated in ER−ve human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 3: The sequence IDs 30 to 42 lists the microRNAs which are significantly up/down regulated in grade 2 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 4: The sequence IDs 43 to 50 lists the microRNAs which are significantly up/down regulated in grade 3 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 5: The sequence IDs 51 to 55 lists the microRNAs which are significantly up/down regulated in stage I of grade 2 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 6: The sequence IDs 56 to 73 lists the microRNAs which are significantly up/down regulated in stage II of grade 2 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 7: The sequence IDs 74 to 81 lists the microRNAs which are significantly up/down regulated in stage III of grade 2 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 8: The sequence IDs 82 to 97 lists the microRNAs which are significantly up/down regulated in stage I of grade 3 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 9: The sequence IDs 98 to 103 lists the microRNAs which are significantly up/down regulated in stage II of grade 3 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 10: The sequence IDs 104 to 107 lists the microRNAs which are significantly up/down regulated in stage III of grade 3 human breast cancer samples. The microRNA names along with their sequences and accession IDs are also described here. The exact fold change with which each microRNA is down regulated (indicated by +ve sign) and those which are upregulated 9 indicated by −Ve sign) are also given.

Table 11: miRNAs validated and reconfirmed by Individual Taqman assays in different grades and stages of Breast cancer spotted on a biochip.

FIG. 1: The sequence IDs 1 to 15 lists the microRNAs which are significantly up/down regulated in ER+ve and non-significant in ER−ve human breast cancer samples. The heat map represents the up and down regulation with respective p values.

FIG. 2: The sequence IDs 16 to 29 lists the microRNAs which are significantly up/down regulated in ER−ve and non-significant in ER+ve human breast cancer samples. The heat map represents the up and down regulation with respective p values.

FIG. 3: The sequence IDs 30 to 42 lists the microRNAs which are significantly up/down regulated in grade 2 and non-significant in grade 3 human breast cancer samples. The heat map represents the up and down regulation with respective p values.

FIG. 4: The sequence IDs 43 to 50 lists the microRNAs which are significantly up/down regulated in grade 3 and non-significant in grade 2 human breast cancer samples. The heat map represents the up and down regulation with respective p values.

FIG. 5: The sequence IDs 51 to 55 lists the microRNAs which are significantly up/down regulated in Stage I of grade 2 and non-significant in stage II and III of grade 2 human breast cancer samples. The heat map represents the up and down regulation with respective p values.

Figure 6:
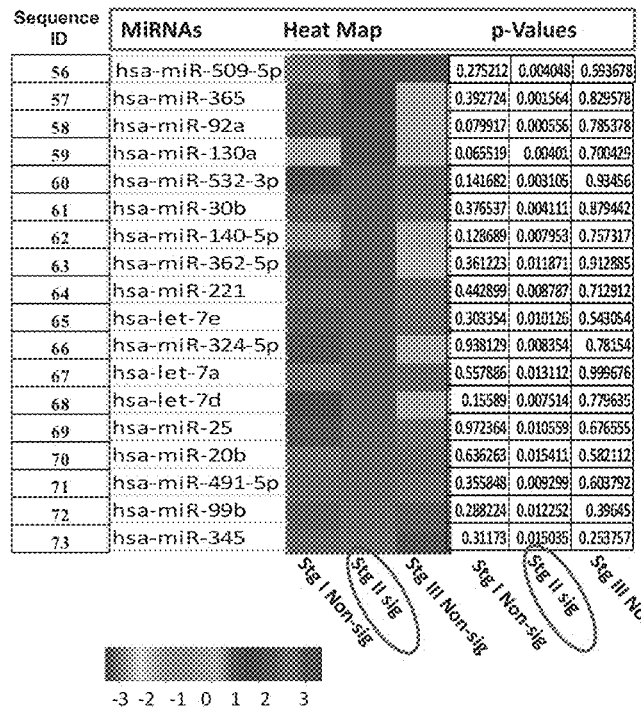

FIG. 6: The sequence IDs 56 to 73 lists the microRNAs which are significantly up/down regulated in Stage II of grade 2 and non-significant in stage I and III of grade 2 human breast cancer samples. The heat map represents the up and down regulation with respective p values.

Figure 7:
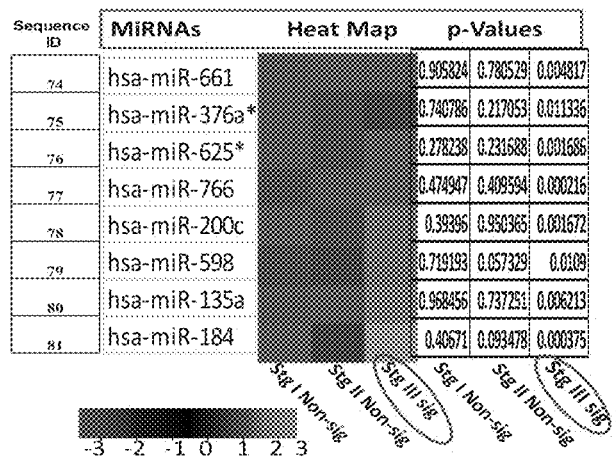

FIG. 7: The sequence IDs 74 to 81 lists the microRNAs which are significantly up/down regulated in Stage III of grade 2 and non-significant in stage I and II of grade 2 human breast cancer samples. The heat map represents the up and down regulation with respective p values.

Figure 8:
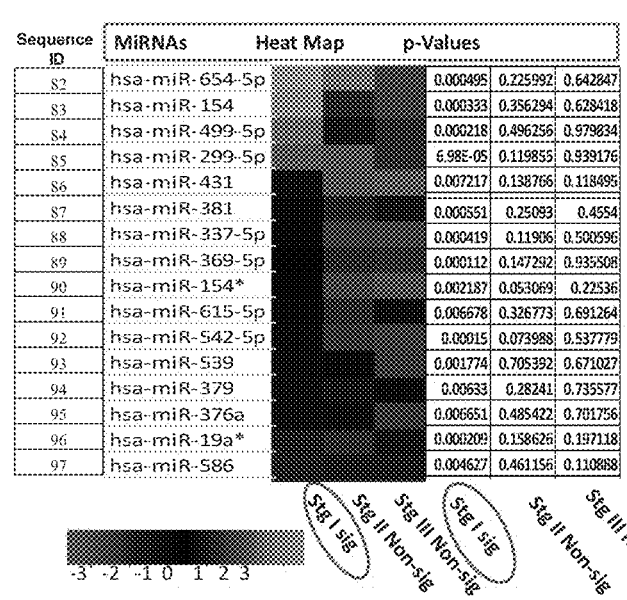

FIG. 8: The sequence IDs 82 to 97 lists the microRNAs which are significantly up/down regulated in Stage I of grade 3 and non-significant in stage II and III of grade 3 human breast cancer samples. The heat map represents the up and down regulation with respective p values.

Figure 9:
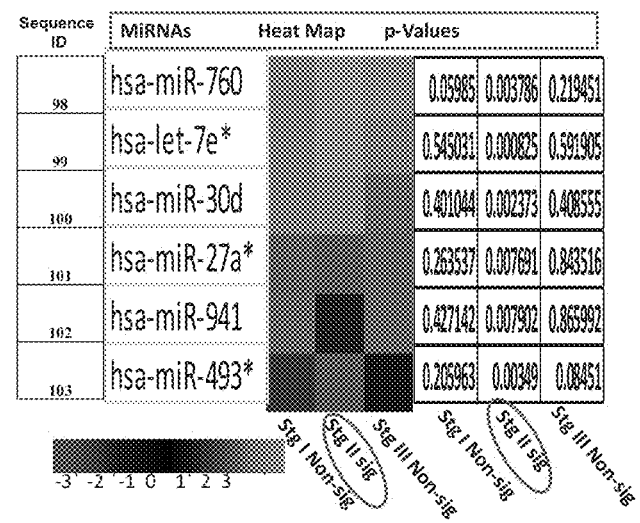

FIG. 9:The sequence IDs 98 to 103 lists the microRNAs which are significantly up/down regulated in Stage II of grade 3 and non-significant in stage I and III of grade 3 human breast cancer samples. The heat map represents the up and down regulation with respective p values.

Figure 10:
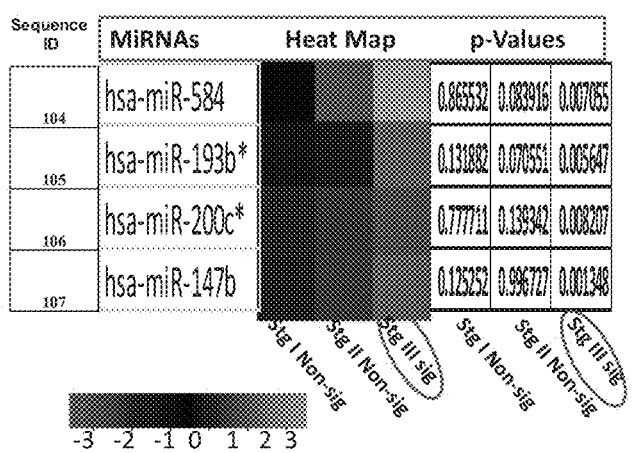

FIG. 10: The sequence IDs 104 to 107 lists the microRNAs which are significantly up/down regulated in Stage III of grade 3 and non-significant in stage I and II of grade 3 human breast cancer samples. The heat map represents the up and down regulation with respective p values.

DETAILED DESCRIPTION OF THE PRESENT INVENTION

Breast cancer is a complex heterogeneous genetic disease, involving a variety of changes in gene expression and structure. MicroRNAs are recently discovered tiny RNA molecules which play an important role in the gene regulation. They are found to have an altered expression in majority of cancers and are termed as oncomiRs. Recently, advances in molecular profiling has shed new light on the etiology of the disease and also acclaimed great potential for the development of novel biomarkers for diagnosis, prognosis and therapeutic targets. This attracts the scientific domain for extensive investigation to further elucidate their precise role as novel biomarkers in malignancy.

MicroRNAs are tiny biological molecules that play a regulatory role in biological processes and cellular functions. Therefore these molecules could be used as indicators of changes in the cells, when they transform from normal to diseased condition. This invention specifically relates to the identification of changes in these small RNA regulations that play an important role in the development of breast cancer. Thus creating an expression signature of these microRNAs involved in cancer (oncomiRs) at particular stages of development or disease progression qualifies them as ideal biomarkers. Thus we have identified changes in the expression pattern of small RNAs called oncomiRs from breast cancer patients at different grades and stages of development of cancer. The expression profile of these miRNAs formed a classic signature, as breast cancer progressed from stage I to stage III, in both grades. These differentially up and down regulated microRNAs are significant in one type, stage and grade of cancer and not in the other. Therefore we have classified them into type, grade and stage specific biomarkers which could be useful tools in the diagnosis and prognosis of breast cancer.

The role of miRNAs as gene regulators distinguishes them as novel biomarkers for diagnosis and prognosis in various cancers. MiRNAs possess unique features that classify them as ideal tumor markers include their tissue specificity, stability, ease of detection and association with the disease status. Thus miRNAs have vast possibility in diagnosis, prognosis and treatment of diseases especially malignancies like breast cancer, where still no reliable tumor markers for particular stages and grades are available at present. Potentially these molecular biomarkers can be used to accurately identify subgroups of patients who will really benefit from cytotoxic chemotherapy with its debilitating side effects. Thus this proves to be an additional, accurate, quick and high throughput molecular diagnostic tool for pathologists especially when patient number is high.

Molecular changes starts in a cell much before morphological changes occur. Our invention has made it possible to detect these early changes, which lead to the initiation and progression of breast cancer. Moreover, large number of samples could be tested at one go in less than 2 hours time, making this a high through put assay and cost effective assay. Finding the deregulated targets of microRNAs has great potential in targeted therapy.

The novelty of these miRNAs is that they detect the early molecular changes in the cell. Thus they are ideal and potential biomarkers for detecting different grades and stages of breast cancer. A few to hundred samples can be checked within a span of 2 to 3 hrs and hence this becomes an easy, fast and high throughput technology.

Though microRNAs are present in the cells and altered signatures are detected and reported in cancer samples, the identification of the different subtype, grade and stage specific microRNAs along with its fold regulation demarcated them as ideal biomarkers for breast cancer diagnosis, prognosis and targeted therapy.

Specific microRNAs are identified by LNA microarray and is verified with Taqman Low Density arrays. The fold regulation of each microRNA was also found by TLDA analysis. Additional validation of these microRNAs were carried out using Taqman individual assays in individual cancer samples and identified for making this as a diagnostic chip (Table 11).

Workflow of miRNA Profiling

RNA was isolated from Breast cancer tissues along with adjacent normals using mirVana™ miRNA Isolation Kit.
1-350 ng total RNA was used for Quantitative Reverse transcriptase reaction.
Megaplex Reverse Transcription rxn (40 cycles) is done using Megaplex RT Primers, (TaqMan® MicroRNA Reverse Transcription Kit) -dNTPs with dTTP, Multiscribe™ reverse Transcriptase, 10× RT Buffer and RNase Inhibitor.
The reverse transcription (RT) reaction was done in a final volume of 7.5 µL which contains: 3 µL total RNA and 4.5 µL of RT reaction mix. Thermocycling condition was set as default and Ramp speed or mode: 9700 using Std or Max ramp.
Preamplification (12 cycles) were done using Megaplex PreAmp Primers, TaqMan® PreAmp Master Mix, 2×.
In this step, pre amplified specific cDNA targets were subjected to increase, the quantity of desired cDNA for miRNA expression analysis using TaqMan® MicroRNA Arrays. The preamplification reaction was performed in a final volume of 25 µL where: 2.5 µL RT product and 22.5 µL PreAmp reaction mix was present.
Real-Time PCR Reaction were done using TaqMan® Universal PCR Master Mix, No AmpErase UNG 2×, TaqMan® MicroRNA Array.
Here the DNA polymerase from the TaqMan® Universal PCR Master Mix amplifies the target cDNA using sequence-specific primers and probe on the TaqMan® MicroRNA Array. The presence of the target is detected in real time through cleavage of the TaqMan probe by the polymerase 5'-3' exonuclease activity.
1. Megaplex RT product and TaqMan Universal PCR Master mix in total volume of 900 µL was mixed.
2. Dispensed 100 µL of the PCR reaction mix into each port of the TaqMan MicroRNA Array centrifuged and then sealed the array.
3. Imported the SDS setup file (SDS.txt) SDS software v2.2 and set for Relative Quantification (ΔΔCt) in 384 well TaqMan Low Density Array.
4. Loaded and ran the array using the 384 well TaqMan Low Density Array default thermal-cycling conditions.

Data Analysis
1. To analyze the results the SDS files were transferred into an RQ study format.
2. Amplification plots, baseline and threshold values were adjusted 3. Threshold cycles (CTs) were compared and analyzed using arithmetic formulas that determines the change in expression of a target gene in an experimental sample relative to the same target in a reference sample. This method was used for high-throughput measurements of relative gene expression.
4. Statminer software was used for fold expression analysis of miRNAs and classified as detector not amplified, significant and nonsignificant based on their p values. Highly significant (≥0.05) miRNAs were selected for study and biomarker identification in the respective types of breast cancer.

EXAMPLES

The following examples are given by way of illustration of the present invention and therefore should not be construed to limit the scope of the present invention.

Example 1

Total RNA Isolation and Quality Control

Tissue samples (100 mg) were homogenized using automated tissue homogenizer and total RNAs were isolated using miRvana kit (Ambion) from all the samples. The quantity of these RNAs was checked using nanodrop and spectophotometer and quality using RIN (RNA Integrity Number) values in Agilent Bioanalyzer. These RNAs were used in all downstream experiments. The reverse transcription reaction was performed using the TaqMan MicroRNA Reverse Transcription Kit followed by Polymerase Chain Reaction. Real-time Polymerase Chain Reaction was performed using an Applied Biosystems 7900-Taqman Low Density Array Real-Time Polymerase Chain Reaction System. Each TaqMan Assay was run in quadruplicate. All the samples displayed good RIN value, linearity (R 2>0.96), good abundance (average CT range 22-28) and NTC (Non-Template Control) CT >38.

Example 2

Taqman Low Density Arrays (TLDA)

MicroRNA profiling was done using TaqManMicroRNA Arrays, which contains megaplex Primer Pools covering Sanger miRBase version 10. Megaplex Reverse Transcription Primers are novel stem-looped RT primer pools that streamline the profiling of hundreds of miRNA targets in a single experiment and reduce the number of Reverse Transcription reactions and the amount of total RNA required for generating a comprehensive miRNA expression profile. A pre amplification step of cDNA with preamp megaplex pool primers was done to significantly enhance the ability to detect slowly expressed miRNAs.

Example 3

Real Time Amplification of miRNA Pool By Loading in TLDA Plates

The TaqMan human MicroRNA arrays consists of 2 plates pool A and pool B. 'A' Array Sanger's V 10.0 contains 667 human taqman microRNA Assays. Three TaqMan MicroRNA Assay. Endogenous controls are included for data normalization and one TaqMan MicroRNA Assay, not related to human is also included as a negative control. The set enables accurate quantitation of 667 human microRNAs.

Results of Taqman Low Density Arrays Analysis

The statistical analysis was performed using statminer software. This contains a filtering procedure for outlier removal; various normalization methods based on single or multiple genes and provides relative quantification analysis of gene expression through a combination of statistical analysis and interactive visualization.

The CT (threshold cycle) values for each well were adjusted and included/excluded for analysis based on the following analysis settings:

if a CT>=Max CT, it was adjusted to Max CT. and calculated the deviation G in units of the standard deviation (SD): G=(max CT−mean CT)/SD. If the following test is true, and (max CT−mean CT)>=0.25, then the replicate with max CT is removed as outlier. Arithmetic Mean uses the arithmetic mean of CT values of the selected controls as the normalization factor (NF), while Geometric Mean uses their geometric mean as the NF. Pearson's product moment correlation coefficient (r) was calculated for CT or ΔCT values of sample pairs, and plotted on the Signal Correlation Plot and Scatter Plot respectively. T-test was performed to calculate p-value. Standard deviation (SD) was calculated for CT values of the technical replicates, and is used to calculate the RQ (fold change).

Based on this analysis, different sets of microRNAs were selected which pertains to different subtypes (ER+ve, ER−ve), grades and stages (Table 1, 2 and 3).

The list of highly significant miRNAs in breast cancer with different types, grades and stages used as novel biomarker for diagnosis and prognosis of breast cancer patient is provided below:

TABLE 1

MicroRNA significantly up/down regulated in ER + ve

| MicroRNAs | Sequence | Accession Id | Fold | Sequence ID |
|---|---|---|---|---|
| hsa-miR-623 | AUCCCUUGCAGGGGCUGUUGGGU | MIMAT0003292 | −40.85544 | 1 |
| hsa-miR-302d | UAAGUGCUUCCAUGUUUGAGUGU | MIMAT0000718 | −34.48034 | 2 |
| hsa-miR-562 | AAAGUAGCUGUACCAUUUGC | MIMAT0003226 | −31.96053 | 3 |
| hsa-miR-224 | CAAGUCACUAGUGGUUCCGUU | MIMAT0000281 | −17.45599 | 4 |
| hsa-miR-452 | AACUGUUUGCAGAGGAAACUGA | MIMAT0001635 | −17.33216 | 5 |
| hsa-miR-522 | AAAAUGGUUCCCUUUAGAGUGU | MIMAT0002868 | −15.13811 | 6 |
| hsa-miR-124 | UAAGGCACGCGGUGAAUGCC | MIMAT0000422 | −12.27811 | 7 |
| hsa-miR-516a-5p | UUCUCGAGGAAAGAAGCACUUUC | MIMAT0004770 | −11.79572 | 8 |
| hsa-miR-521 | AACGCACUUCCCUUUAGAGUGU | MIMAT0002854 | −10.90129 | 9 |
| hsa-miR-627 | GUGAGUCUCUAAGAAAAGAGGA | MIMAT0003296 | −4.234165 | 10 |
| hsa-miR-650 | AGGAGGCAGCGCUCUCAGGAC | MIMAT0003320 | −3.254617 | 11 |
| hsa-miR-205 | UCCUUCAUUCCACCGGAGUCUG | MIMAT0000266 | −3.148418 | 12 |
| hsa-miR-605 | UAAAUCCCAUGGUGCCUUCUCCU | MIMAT0003273 | 13.311642 | 13 |
| hsa-miR-375 | UUUGUUCGUUCGGCUCGCGUGA | MIMAT0000728 | 13.609262 | 14 |
| hsa-miR-190b | UGAUAUGUUUGAUAUUGGGUU | MIMAT0004929 | 40.579717 | 15 | pvalue 0.01-2.40E-14

TABLE 2

MicroRNA significantly up/down regulated in ER − ve

| MicroRNAs | Sequence | Accession Id | Fold | Sequence ID |
|---|---|---|---|---|
| hsa-miR-887 | GUGAACGGGCGCCAUCCCGAGG | MIMAT0004951 | −10.90658 | 16 |
| hsa-miR-126* | CAUUAUUACUUUUGGUACGCG | MIMAT0000444 | −3.717792 | 17 |
| hsa-miR-188-5p | CAUCCCUUGCAUGGUGGAGGG | MIMAT0000457 | 2.600684 | 18 |
| hsa-miR-210 | CUGUGCGUGUGACAGCGGCUGA | MIMAT0000267 | 3.6747714 | 19 |
| hsa-miR-20a | UAAAGUGCUUAUAGUGCAGGUAG | MIMAT0000075 | 3.8147056 | 20 |
| hsa-miR-31 | AGGCAAGAUGCUGGCAUAGCU | MIMAT0000089 | 4.1211402 | 21 |

TABLE 2 -continued

MicroRNA significantly up/down regulated in ER - ve

| MicroRNAs | Sequence | Accession Id | Fold | Sequence ID |
|---|---|---|---|---|
| hsa-miR-187 | UCGUGUCUUGUGUUGCAGCCGG | MIMAT0000262 | 4.6737121 | 22 |
| hsa-miR-301b | CAGUGCAAUGAUAUUGUCAAAGC | MIMAT0004958 | 5.6936425 | 23 |
| hsa-miR-142-3p | UGUAGUGUUUCCUACUUUAUGGA | MIMAT0000434 | 5.9133475 | 24 |
| hsa-miR-18a | UAAGGUGCAUCUAGUGCAGAUAG | MIMAT0000072 | 6.9884545 | 25 |
| hsa-miR-137 | UUAUUGCUUAAGAAUACGCGUAG | MIMAT0000429 | 7.8730989 | 26 |
| hsa-miR-9 | UCUUUGGUUAUCUAGCUGUAUGA | MIMAT0000441 | 8.1181347 | 27 |
| hsa-miR-135b* | AUGUAGGGCUAAAAGCCAUGGG | MIMAT0004698 | 8.6834163 | 28 |
| hsa-miR-934 | UGUCUACUACUGGAGACACUGG | MIMAT0004977 | 15.642491 | 29 | pvalue 0.01-0.00098

TABLE 3

MicroRNA significantly up/down regulated in Grade 2

| MicroRNAs | Sequence | Accession Id | Fold | Sequence ID |
|---|---|---|---|---|
| hsa-miR-143* | GGUGCAGUGCUGCAUCUCUGGU | MIMAT0004599 | -78.86936 | 30 |
| hsa-miR-361-3p | UCCCCCAGGUGUGAUUCUGAUUU | MIMAT0004682 | -20.75945 | 31 |
| hsa-miR-129-3p | AAGCCCUUACCCCAAAAAGCAU | MIMAT0004605 | -10.96402 | 32 |
| hsa-miR-561 | CAAAGUUUAAGAUCCUUGAAGU | MIMAT0003225 | -4.984571 | 33 |
| hsa-miR-548b-5p | AAAAGUAAUUGUGGUUUUGGCC | MIMAT0004798 | -4.389338 | 34 |
| hsa-miR-627 | GUGAGUCUCUAAGAAAAGAGGA | MIMAT0003296 | -4.370396 | 35 |
| hsa-miR-92a-1* | AGGUUGGGAUCGGUUGCAAUGCU | MIMAT0004507 | -1.840965 | 36 |
| hsa-miR-93* | ACUGCUGAGCUAGCACUUCCCG | MIMAT0004509 | 1.4612617 | 37 |
| hsa-miR-571 | UGAGUUGGCCAUCUGAGUGAG | MIMAT0003236 | 2.2381639 | 38 |
| hsa-miR-7-1* | CAACAAAUCACAGUCUGCCAUA | MIMAT0004553 | 2.4298469 | 39 |
| hsa-miR-26a-2* | CCUAUUCUUGAUUACUUGUUUC | MIMAT0004681 | 2.9292837 | 40 |
| hsa-miR-449b | AGGCAGUGUAUUGUUAGCUGGC | MIMAT0003327 | 10.183938 | 41 |
| hsa-miR-449a | UGGCAGUGUAUUGUUAGCUGGU | MIMAT0001541 | 16.080831 | 42 | pvalue 0.01-9.09E-06

TABLE 4

MicroRNA significantly up/down regulated in Grade 3

| MicroRNAs | Sequence | Accession Id | Fold | Sequence ID |
|---|---|---|---|---|
| hsa-miR-195* | CCAAUAUUGGCUGUGCUGCUCC | MIMAT0004615 | -230.2186 | 43 |
| hsa-miR-567 | AGUAUGUUCUUCCAGGACAGAAC | MIMAT0003231 | -11.57537 | 44 |
| hsa-miR-29c* | UGACCGAUUUCUCCUGGUGUUC | MIMAT0004673 | -4.963266 | 45 |
| hsa-miR-30e* | CUUUCAGUCGGAUGUUUACAGC | MIMAT0000693 | -3.293634 | 46 |

TABLE 4 -continued

MicroRNA significantly up/down regulated in Grade 3

| MicroRNAs | Sequence | Accession Id | Fold | Sequence ID |
|---|---|---|---|---|
| hsa-miR-30a* | CUUUCAGUCGGAUGUUUGCAGC | MIMAT0000088 | -3.10055 | 47 |
| hsa-miR-29b-2* | CUGGUUUCACAUGGUGGCUUAG | MIMAT0004515 | -2.687606 | 48 |
| hsa-miR-135b | UAUGGCUUUUCAUUCCUAUGUGA | MIMAT0000758 | 6.416591 | 49 |
| hsa-miR-767-5p | UGCACCAUGGUUGUCUGAGCAUG | MIMAT0003882 | 101.53822 | 50 | pvalue 0.01-8.5E-07

TABLE 5

MicroRNA significantly up/down regulated in Grade 2 Stage I

| MicroRNAs | Sequence | Accession Id | Fold | Sequence ID |
|---|---|---|---|---|
| hsa-miR-874 | CUGCCCUGGCCCGAGGGACCGA | MIMAT0004911 | -86.318 | 51 |
| hsa-miR-487a | AAUCAUACAGGGACAUCCAGUU | MIMAT0002178 | -41.49081 | 52 |
| hsa-miR-655 | AUAAUACAUGGUUAACCUCUUU | MIMAT0003331 | -13.23111 | 53 |
| hsa-miR-30d* | CUUUCAGUCAGAUGUUUGCUGC | MIMAT0004551 | -6.504431 | 54 |
| hsa-miR-136 | ACUCCAUUUGUUUUGAUGAUGGA | MIMAT0000448 | -6.321441 | 55 | pvalue 0.0067-0.003

TABLE 6

MicroRNA significantly up/down regulated in Grade 2 Stage II

| MicroRNAs | Sequence | Accession Id | Fold | Sequence ID |
|---|---|---|---|---|
| hsa-miR-509-5p | UACUGCAGACAGUGGCAAUCA | MIMAT0004779 | -34.51461 | 56 |
| hsa-miR-365 | UAAUGCCCCUAAAAAUCCUUAU | MIMAT0000710 | -8.811865 | 57 |
| hsa-miR-92a | UAUUGCACUUGUCCCGGCCUGU | MIMAT0000092 | -8.117638 | 58 |
| hsa-miR-130a | CAGUGCAAUGUUAAAAGGGCAU | MIMAT0000425 | -8.054065 | 59 |
| hsa-miR-532-3p | CAUGCCUUGAGUGUAGGACCGU | MIMAT0002888 | -6.646912 | 60 |
| hsa-miR-30b | UGUAAACAUCCUACACUCAGCU | MIMAT0000420 | -6.620686 | 61 |
| hsa-miR-140-5p | CAGUGGUUUUACCCUAUGGUAG | MIMAT0000431 | -6.46631 | 62 |
| hsa-miR-362-5p | AAUCCUUGGAACCUAGGUGUGAGU | MIMAT0000705 | -6.386795 | 63 |
| hsa-miR-221 | AGCUACAUUGUCUGCUGGGUUUC | MIMAT0000278 | -6.37909 | 64 |
| hsa-let-7e | UGAGGUAGGAGGUUGUAUAGUU | MIMAT0000066 | -6.094803 | 65 |
| hsa-miR-324-5p | CGCAUCCCCUAGGGCAUUGGUGU | MIMAT0000761 | -6.072664 | 66 |
| hsa-let-7a | UGAGGUAGUAGGUUGUAUAGUU | MIMAT0000062 | -5.936147 | 67 |
| hsa-let-7d | AGAGGUAGUAGGUUGCAUAGUU | MIMAT0000065 | -5.833018 | 68 |
| hsa-miR-25 | CAUUGCACUUGUCUCGGUCUGA | MIMAT0000081 | -5.692002 | 69 |
| hsa-miR-20b | CAAAGUGCUCAUAGUGCAGGUAG | MIMAT0001413 | -5.261795 | 70 |
| hsa-miR-491-5p | AGUGGGGAACCCUUCCAUGAGG | MIMAT0002807 | -4.981938 | 71 |

TABLE 6 -continued

MicroRNA significantly up/down regulated in Grade 2 Stage II

| MicroRNAs | Sequence | Accession Id | Fold | Sequence ID |
|---|---|---|---|---|
| hsa-miR-99b | CACCCGUAGAACCGACCUUGCG | MIMAT0000689 | -4.539054 | 72 |
| hsa-miR-345 | GCUGACUCCU AGUCCAGGGC UC | MIMAT0000825 | -3.639054 | 73 | pvalue 0.01-0.00055

TABLE 7

MicroRNA significantly up/down regulated in Grade 2 Stage III

| MicroRNAs | Sequence | Accession Id | Fold | Sequence ID |
|---|---|---|---|---|
| hsa-miR-661 | UGCCUGGGUCUCUGGCCUGCGCGU | MIMAT0003324 | -72.56704 | 74 |
| hsa-miR-376a* | GUAGAUUCUCCUUCUAUGAGUA | MIMAT0003386 | -4.924847 | 75 |
| hsa-miR-625* | GACUAUAGAACUUUCCCCCUCA | MIMAT0004808 | 1.6739604 | 76 |
| hsa-miR-766 | ACUCCAGCCCCACAGCCUCAGC | MIMAT0003888 | 1.7897822 | 77 |
| hsa-miR-200c | UAAUACUGCCGGGUAAUGAUGGA | MIMAT0000617 | 5.6291585 | 78 |
| hsa-miR-598 | UACGUCAUCGUUGUCAUCGUCA | MIMAT0003266 | 6.1447238 | 79 |
| hsa-miR-135a | UAUGGCUUUUUAUUCCUAUGUGA | MIMAT0000428 | 9.0314152 | 80 |
| hsa-miR-184 | UGGACGGAGAACUGAUAAGGGU | MIMAT0000454 | 22.902401 | 81 | pvalue 0.01-0.00037

TABLE 8

MicroRNA significantly up/down regulated in Grade 3 Stage I

| MicroRNAs | Sequence | Accession Id | Fold | Sequence ID |
|---|---|---|---|---|
| hsa-miR-654-5p | UGGUGGGCCGCAGAACAUGUGC | MIMAT0003330 | -61.18959 | 82 |
| hsa-miR-154 | UAGGUUAUCCGUGUUGCCUUCG | MIMAT0000452 | -55.31606 | 83 |
| hsa-miR-499-5p | UUAAGACUUGCAGUGAUGUUU | MIMAT0002870 | -42.64146 | 84 |
| hsa-miR-299-5p | UGGUUUACCGUCCCACAUACAU | MIMAT0002890 | -37.59992 | 85 |
| hsa-miR-431 | UGUCUUGCAGGCCGUCAUGCA | MIMAT0001625 | -16.19831 | 86 |
| hsa-miR-381 | UAUACAAGGGCAAGCUCUCUGU | MIMAT0000736 | -13.54713 | 87 |
| hsa-miR-337-5p | GAACGGCUUCAUACAGGAGUU | MIMAT0004695 | -13.22481 | 88 |
| hsa-miR-369-5p | AGAUCGACCGUGUUAUAUUCGC | MIMAT0001621 | -10.50421 | 89 |
| hsa-miR-154* | AAUCAUACACGGUUGACCUAUU | MIMAT0000453 | -9.909352 | 90 |
| hsa-miR-615-5p | GGGGGUCCCCGGUGCUCGGAUC | MIMAT0004804 | -8.392234 | 91 |
| hsa-miR-542-5p | UCGGGGAUCAUCAUGUCACGAGA | MIMAT0003340 | -7.18576 | 92 |
| hsa-miR-539 | GGAGAAAUUAUCCUUGGUGUGU | MIMAT0003163 | -4.765181 | 93 |
| hsa-miR-379 | UGGUAGACUAUGGAACGUAGG | MIMAT0000733 | -3.923594 | 94 |
| hsa-miR-376a | AUCAUAGAGGAAAAUCCACGU | MIMAT0000729 | -3.799978 | 95 |

TABLE 8 -continued

MicroRNA significantly up/down regulated in Grade 3 Stage I

| MicroRNAs | Sequence | Accession Id | Fold | Sequence ID |
|---|---|---|---|---|
| hsa-miR-19a* | AGUUUUGCAUAGUUGCACUACA | MIMAT0004490 | 8.2999188 | 96 |
| hsa-miR-586 | UAUGCAUUGUAUUUUAGGUCC | MIMAT0003252 | 9.2991122 | 97 |

TABLE 9

MicroRNA significantly up/down regulated in Grade 3 Stage II

| MicroRNAs | Sequence | Accession Id | Fold | Sequence ID |
|---|---|---|---|---|
| hsa-miR-760 | CGGCUCUGGGUCUGUGGGGA | MIMAT0004957 | -5.391269 | 98 |
| hsa-let-7e* | CUAUACGGCCUCCUAGCUUUCC | MIMAT0004485 | -1.33367 | 99 |
| hsa-miR-30d | UGUAAACAUCCCCGACUGGAAG | MIMAT0000245 | -1.683826 | 100 |
| hsa-miR-27a* | AGGGCUUAGCUGCUUGUGAGCA | MIMAT0004501 | 1.3726469 | 101 |
| hsa-miR-941 | CACCCGGCUGUGUGCACAUGUGC | MIMAT0004984 | 1.4397387 | 102 |
| hsa-miR-493* | UUGUACAUGGUAGGCUUUCAUU | MIMAT0002813 | 1.9122828 | 103 | pvalue 0.0023-0.00085

TABLE 10

MicroRNA significantly up/down regulated in Grade 3 Stage III

| MicroRNAs | Sequence | Accession Id | Fold | Sequence ID |
|---|---|---|---|---|
| hsa-miR-584 | UUAUGGUUUGCCUGGGACUGAG | MIMAT0003249 | -13.69725 | 104 |
| hsa-miR-193b* | CGGGGUUUUGAGGGCGAGAUGA | MIMAT0004767 | -8.708156 | 105 |
| hsa-miR-200c* | CGUCUUACCCAGCAGUGUUUGG | MIMAT0004657 | 6.7748051 | 106 |
| hsa-miR-147b | GUGUGCGGAAAUGCUUCUGCUA | MIMAT0004928 | 12.909898 | 107 | pvalue 0.008-0.001

Example 4

LNA Microarray

The differentially expressed microRNAs identified by Taqman Low Density Arrays were further confirmed with LNA (Locked Nucleic Acid) Array. The RNA isolated from the same cancer samples were hybridized against 2002 microRNAs consisting of 904 human, 388 rat and 710 mouse microRNAs. The normals were labeled with Hy5 dye and samples were labeled with Hy3 and also reversely hybridised and taken the mean intensities for calculation.

The normalized median signal intensities for the Hy3 (sample) and Hy5 (common reference) indicate the relative expression level of each microRNA in the samples and in the common reference. If the Hy3 value is higher than the Hy5 value there is a higher expression in the sample than in the common reference and if the Hy3 value is lower than that of Hy5 value there is a lower expression in the samples compared to the common reference. Then we take the ratios between the Hy3 and Hy5 signal and the log 2 to that ratio. A positive number indicates a higher expression in the sample (Hy3) compared to the common reference and vice versa. The NA means that the microRNA is not expressed based on certain cut-off criteria. One criterion is the signal intensity of the Hy3 and Hy5 channel. If both Hy3 and Hy5 signals are below 1.5 times the median of all capture probes on the array we say that it is background and below our cut-off. This cut-off is set to avoid too many false positives.

Call rate is the number of expressed microRNAs compared to the total number of microRNAs analyzed (the % of identified microRNAs). This call rate is expected to be between 20 and 50% for human samples and it is clear that we have a very nice and high call rate in our samples. That human samples have call rates between 20 and 50% has been documented in the literature, both based on deep sequencing, array and PCR profiling. A call rate much higher than 50% indicates a high risk of having false positives in the data set Therefore we used the 1.5× median of all capture probes as a cut off.

The microRNAs have been analyzed based on the samples groups. A two-tailed statistical t-test has been performed between the samples groups grade 2 and grade 3. The heat map has been made based on a cut-off of $P<10^{-3}$. "Expression matrix (analysis)" looked like typical breast cancer microRNAs. A very long list of breast cancer miRNAs from literature, web databases are all present in our samples. Just to mention some examples, miR-21, miR-155, miR-148a, miR 210 and miR-29b. These typical breast cancer signatures clearly classify our samples as breast cancer samples.

The identification of miRNAs in particular stages or grades shows its behavior which is highly correlated with the expression of translational regulators or targets that are involved in tumor progression. The miRNAs which are down regulated at stage I, gets up or down regulated successively at stage II and stage III with in a grade. This classical pattern of miRNA expression indicates their importance in controlling the progressive growth of breast cancer.

The findings of these significant novel miRNAs in specific stages and grades will enable us to design individual assays for their validation in vitro and invivo. These validated miRNAs may give new insight for the diagnosis and treatment of tumor, progressing at specific stages or grades.

Furthermore, these differentially up/down regulated miRNAs in various stages of breast cancer identified by TLDA technique, have also been confirmed by LNA microarry technology. This also reconfirms the trend of expression pattern in aforesaid stages and grades of breast cancer. These finding indicated that the expression of common miRNAs in both the techniques have some defined role in the tumor progression. Among these common miRNAs, few highly up/down ones are selected for their individual assay validation is been done to prove these candidate miRNAs as novel biomarker for particular grade/stage of breast cancer.

Example 5

Validation of Highly Up/Down Regulated MicroRNAs By Q-per

Six of the highly up and down regulated category of microRNAs which are common among the TLDA microarray and LNA microarray were selected for its further validation among the rest of individual samples in grade 2 and grade 3 by q-per analysis. (Table 11)

Advantages

These novel biomarkers could be developed as a diagnostic kit for early and accurate diagnosis of human breast cancer. They are direct indicators of cellular changes during the initiation and development of breast cancer. These biomarkers complement the pathologists for the accurate grading and staging of breast cancer. These biomarkers provided a utility angle to the already existing biological molecules called microRNAs which play a major role in gene regulation. These biomarkers could provide a fast, cheaper, accurate, robust and high throughput diagnostic kit for accurate diagnosis of human breast cancer.

TABLE 11 miRNAs validated and reconfirmed by Individual Taqman assays in different grades and stages of Breast cancer spotted on a biochip.

| | Fold Individual Taqman assay | | Up/Down Taqman Low Density Array | |
|---|---|---|---|---|
| ER − ve | | | | |
| miR-9 | ↑ | 11.4 | ↑ | 7.8 |
| miR-135b* | ↑ | 10.4 | ↑ | 8.1 |
| miR-137 | ↑ | 181.4 | ↑ | 8.6 |
| ER + ve | | | | |
| miR-605 | ↑ | 6.6 | ↑ | 13.3 |
| miR-375 | ↑ | 48.4 | ↑ | 13.6 |
| miR-190b | ↑ | 135.1 | ↑ | 40.5 |
| GR 2 | | | | |
| miR-7-1* | ↑ | 5.6 | ↑ | 2.9 |
| miR-449a | ↑ | 19.4 | ↑ | 16.1 |
| miR-449b | ↑ | 23.0 | ↑ | 10.8 |
| GR 3 | | | | |
| miR-135b | ↑ | 70.3 | ↑ | 6.4 |
| miR-767-5p | ↑ | 22.8 | ↑ | 101.5 |
| GR 2Stg I | | | | |
| miR-487a | ↓ | −2.4 | ↓ | −41.4 |
| miR-655 | ↓ | −3.5 | ↓ | −13.2 |
| miR-874 | ↓ | −2.0 | ↓ | −86.3 |
| GR 2Stg II | | | | |
| let-7d | ↓ | −7.6 | ↓ | −5.8 |
| miR-365 | ↓ | −11.4 | ↓ | −8.8 |
| GR 2Stg III | | | | |
| miR-135a | ↑ | 6.6 | ↑ | 9.1 |
| miR-200c | ↑ | 7.2 | ↑ | 5.6 |
| miR-184 | ↑ | 26.2 | ↑ | 22.9 |
| GR 3Stg I | | | | |
| miR-19a* | ↑ | 2.8 | ↑ | 8.2 |
| miR-586 | ↑ | 4.2 | ↑ | 9.2 |
| miR-654-5p | ↓ | −2.1 | ↓ | −61.1 |
| GR 3Stg II | | | | |
| miR-30d | ↓ | −1.6 | ↓ | −1.6 |
| miR-493* | ↑ | 4.3 | ↑ | 1.9 |
| miR-941 | ↑ | 3.5 | ↑ | 1.4 |
| GR 3Stg III | | | | |
| miR-193b* | ↓ | −2.5 | ↓ | −8.7 |
| miR-584 | ↓ | −3.7 | ↓ | −13.7 |
| miR-200c* | ↑ | 1.7 | ↑ | 6.7 |
| miR-147b | ↑ | 17.8 | ↑ | 12.9 |

REFERENCES

1. Brennecke J, Hipfner D R, Stark A, Russell R B, Cohen S M: bantam encodes a developmentally regulated microRNA that controls cell proliferation and regulates the proapoptotic gene hid in *Drosophila*. Cell 2003, 113:25-36.

2. Lee R C, Feinbaum R L, Ambros V: The *C. elegans* heterochronic gene lin-4 encodes small RNAs with antisense complementarity to lin-14. Cell 1993, 75:843-854.

3. Calin G A, Liu C G, Sevignani C, Ferracin M, Felli N, Dumitru C D, Shimizu M, Cimmino A, Zupo S, Dono M, Dell'Aquila M L, Alder H, Rassenti L, Kipps T J, Bullrich F, Negrini M, Croce C M: MicroRNA profiling reveals distinct signatures in B cell chronic lymphocytic leukemias. Proc Natl Acad Sci USA 2004, 101:11755-11760.

4. Calin G A, Croce C M: MicroRNA signatures in human cancers. Nat Rev Cancer 2006, 6:857-866.41. Scott G K, Goga A, Bhaumik D, Berger C E, Sullivan C S, Benz C C: Coordinate suppression of ERBB2 and ERBB3 by enforced expression of micro-RNA miR-125a or miR-125b. J Biol Chem 2007, 282:1479-1486.

5. Lu J, Getz G, Miska E A, Alvarez-Saavedra E, Lamb J, Peck D, Sweet-Cordero A, Ebert B L, Mak R H, Ferrando A A, Downing J R, Jacks T, Horvitz H R, Golub T R: MicroRNA expression profiles classify human cancers. Nature 2005, 435:834-838. non-small cell lung cancer. Cancer Res 2006, 66:5338-5345.

6. Iorio M V, Ferracin M, Liu C G, Veronese A, Spizzo R, Sabbioni S, Magri E, Pedrialic M, Fabbri M, Campiglio M, Ménard S, Palazzo J P, Rosenberg A, Musiani P, cVolinia S, Nenci I, Calin G A, Querzoli P, Negrini M, Croce C M: MicroRNA gene expression deregulation in human breast cancer. Cancer Res 2005, 65:7065-7070. polarity in cancer. Cancer Res 2008, 68:537-544.

7. Adams B D, Furneaux H, and White B A: The micro-ribonucleic acid (miRNA) miR-206 targets the human estrogen receptor-alpha (ERalpha) and represses ERalpha messenger RNA and protein expression in breast cancer cell lines. Mol Endocrinol 2007, 21:1132-1147.

8. Yu Z, Wang C, Wang M, Li Z, Casimiro M C, Liu M, Wu K, Whittle J, Ju X, Hyslop T, McCue P, Pestell R G: A cyclin D1/microRNA 17/20 regulatory feedback loop in control of breast cancer cell proliferation. J Cell Biol 2008, 182:509-517.

9. Mattie M D, Benz C C, Bowers J, Sensinger K, Wong L, Scott G K, Fedele V, Ginzinger D, Getts R, Haqq C: Optimized high-throughput microRNA expression profiling provides novel biomarker assessment of clinical prostate and breast cancer biopsies. Mol Cancer 2006, 5:24.

10. Thiery J P, Acloque H, Huang R Y J, and Nieto M A: Epithelial-mesenchymal transitions in development and disease. Cell 2009, 139:871-890.

11. Yu F, Yao H, Zhu P, Zhang X, Pan Q, Gong C, Huang Y, Hu X, Su F, Lieberman J, Song E: let-7 regulates self renewal and tumorigenicity of breast cancer cells. Cell 2007, 131:1109-1123.

12. Zhu S, Si M-L, Wu H, Mo Y-Y: MicroRNA-21 targets the tumor suppressor gene tropomyosin 1 (TPM1). *J Biol Chem* 2007, 282:14328-14336.

13. Kong W, Yang H, He L, Zhao J-j, Coppola D, Dalton W S, and Cheng J Q: MicroRNA-155 is regulated by the transforming growth factor beta/Smad pathway and contributes to epithelial cell plasticity by targeting RhoA. *Mol Cell Biol* 2008, 28:6773-6784.

14. Ma L, Teruya-Feldstein J, Weinberg R A: Tumour invasion and metastasis initiated by microRNA-10b in breast cancer. *Nature* 2007, 449:682-688.

15. Radojicic Jelena J, Zaravinos Apostolos A, Vrekoussis Thomas T, Kafousi Maria M, Spandidos Demetrios A DA, Stathopoulos Efstathios N EN.microRNA expression analysis in triple-negative (ER, PR and Her2/neu) breast cancer. Cell cycle (Georgetown, Tex.) 10(3), 2011

We claim:

1. A microarray consisting of a panel of probes for miRNAs affixed to the microarray, which panel is useful for screening and detection for the type, grade and stage of breast cancer, wherein the miRNAs consist of SEQ ID Nos. 1-107, or a subset thereof consisting of SEQ ID Nos. 30-42 or SEQ ID Nos. 51-55.

2. The panel as claimed in claim 1, wherein SEQ ID Nos. 30-42 detect grade 2 breast cancer.

3. The panel as claimed in claim 1, wherein SEQ ID Nos. 51-55 detect stage I of grade 2 breast cancer.

4. A kit for detecting type, grade and stage of breast cancer wherein the kit consists of:

I. a microarray as claimed in claim 1,
II. suitable reagents capable of detecting singly or a combination of the miRNA; and
III. an instruction manual for using the kit.

5. An in vitro non-invasive method using the panel as claimed in claim 1 for detecting the type, grade and stage of breast cancer in a human subject, comprising:

hybridizing a breast tissue sample comprising RNA or cDNA of the RNA from a human with the microarray of claim 1, wherein the sample is suspected of having breast cancer cells; and detecting the type, grade and/or stage of breast cancer based on the relative level and profile of hybridization to the panel of probes in the microarray, wherein the type detected is estrogen receptor positive or estrogen receptor negative, wherein the grade detected is grade 2 or grade 3, and wherein the stage detected is stage I, stage II or stage III.

6. The method as claimed in claim 5, wherein SEQ ID Nos. 30-42 detect grade 2 breast cancer.

7. The method as claimed in claim 5, wherein SEQ ID Nos. 51-55 detect stage 1 grade 2 breast cancer.

* * * * *

SEQUENCE LISTING

```
<160> NUMBER OF SEQ ID NOS: 107

<210> SEQ ID NO 1
<211> LENGTH: 23
<212> TYPE: RNA
<213> ORGANISM: homo sapiens
<220> FEATURE:
<223> OTHER INFORMATION: miRNA : hsa-miR-623

<400> SEQUENCE: 1
aucccuugca ggggcuguug ggu                                        23

<210> SEQ ID NO 2
<211> LENGTH: 23
<212> TYPE: RNA
<213> ORGANISM: homo sapiens
<220> FEATURE:
<223> OTHER INFORMATION: miRNA: hsa-miR-302d

<400> SEQUENCE: 2
uaagugcuuc cauguuugag ugu                                        23

<210> SEQ ID NO 3
<211> LENGTH: 20
<212> TYPE: RNA
<213> ORGANISM: homo sapiens
<220> FEATURE:
<223> OTHER INFORMATION: miRNA: hsa-miR-562

<400> SEQUENCE: 3
aaaguagcug uaccauuugc                                            20

<210> SEQ ID NO 4
```

```
<211> LENGTH: 21
<212> TYPE: RNA
<213> ORGANISM: homo sapiens
<220> FEATURE:
<223> OTHER INFORMATION: miRNA: hsa-miR-224

<400> SEQUENCE: 4
caagucacua gugguuccgu u                                              21

<210> SEQ ID NO 5
<211> LENGTH: 22
<212> TYPE: RNA
<213> ORGANISM: homo sapiens
<220> FEATURE:
<223> OTHER INFORMATION: miRNA: hsa-miR-452

<400> SEQUENCE: 5
aacuguuugc agaggaaacu ga                                             22

<210> SEQ ID NO 6
<211> LENGTH: 22
<212> TYPE: RNA
<213> ORGANISM: homo sapiens
<220> FEATURE:
<223> OTHER INFORMATION: miRNA: hsa-miR-522

<400> SEQUENCE: 6
aaaaugguuc ccuuuagagu gu                                             22

<210> SEQ ID NO 7
<211> LENGTH: 20
<212> TYPE: RNA
<213> ORGANISM: homo sapiens
<220> FEATURE:
<223> OTHER INFORMATION: miRNA: hsa-miR-124

<400> SEQUENCE: 7
uaaggcacgc ggugaaugcc                                                20

<210> SEQ ID NO 8
<211> LENGTH: 23
<212> TYPE: RNA
<213> ORGANISM: homo sapiens
<220> FEATURE:
<223> OTHER INFORMATION: miRNA: hsa-miR-516a-5p

<400> SEQUENCE: 8
uucucgagga aagaagcacu uuc                                            23

<210> SEQ ID NO 9
<211> LENGTH: 22
<212> TYPE: RNA
<213> ORGANISM: homo sapiens
<220> FEATURE:
<223> OTHER INFORMATION: miRNA: hsa-miR-521

<400> SEQUENCE: 9
aacgcacuuc ccuuuagagu gu                                             22

<210> SEQ ID NO 10
<211> LENGTH: 22
<212> TYPE: RNA
<213> ORGANISM: homo sapiens
<220> FEATURE:
<223> OTHER INFORMATION: miRNA: hsa-miR-627

<400> SEQUENCE: 10
```

-continued gugagucucu aagaaaagag ga					22

<210> SEQ ID NO 11
<211> LENGTH: 21
<212> TYPE: RNA
<213> ORGANISM: homo sapiens
<220> FEATURE:
<223> OTHER INFORMATION: miRNA: hsa-miR-650

<400> SEQUENCE: 11
aggaggcagc gcucucagga c					21

<210> SEQ ID NO 12
<211> LENGTH: 22
<212> TYPE: RNA
<213> ORGANISM: homo sapiens
<220> FEATURE:
<223> OTHER INFORMATION: miRNA: hsa-miR-205

<400> SEQUENCE: 12
uccuucauuc caccggaguc ug					22

<210> SEQ ID NO 13
<211> LENGTH: 23
<212> TYPE: RNA
<213> ORGANISM: homo sapiens
<220> FEATURE:
<223> OTHER INFORMATION: miRNA: hsa-miR-605

<400> SEQUENCE: 13
uaaaucccau ggugccuucu ccu					23

<210> SEQ ID NO 14
<211> LENGTH: 22
<212> TYPE: RNA
<213> ORGANISM: homo sapiens
<220> FEATURE:
<223> OTHER INFORMATION: miRNA: hsa-miR-375

<400> SEQUENCE: 14
uuuguucguu cggcucgcgu ga					22

<210> SEQ ID NO 15
<211> LENGTH: 21
<212> TYPE: RNA
<213> ORGANISM: homo sapiens
<220> FEATURE:
<223> OTHER INFORMATION: miRNA: hsa-miR-190b

<400> SEQUENCE: 15
ugauauguuu gauauugggu u					21

<210> SEQ ID NO 16
<211> LENGTH: 22
<212> TYPE: RNA
<213> ORGANISM: homo sapiens
<220> FEATURE:
<223> OTHER INFORMATION: miRNA: hsa-miR-887

<400> SEQUENCE: 16
gugaacgggc gccaucccga gg					22

<210> SEQ ID NO 17
<211> LENGTH: 21
<212> TYPE: RNA

```
<213> ORGANISM: homo sapiens
<220> FEATURE:
<223> OTHER INFORMATION: miRNA: hsa-miR-126*

<400> SEQUENCE: 17
cauuauuacu uuugguacgc g                                          21

<210> SEQ ID NO 18
<211> LENGTH: 21
<212> TYPE: RNA
<213> ORGANISM: homo sapiens
<220> FEATURE:
<223> OTHER INFORMATION: miRNA: hsa-miR-188-5p

<400> SEQUENCE: 18
caucccuugc augguggagg g                                          21

<210> SEQ ID NO 19
<211> LENGTH: 22
<212> TYPE: RNA
<213> ORGANISM: homo sapiens
<220> FEATURE:
<223> OTHER INFORMATION: miRNA: hsa-miR-210

<400> SEQUENCE: 19
cugugcgugu gacagcggcu ga                                         22

<210> SEQ ID NO 20
<211> LENGTH: 23
<212> TYPE: RNA
<213> ORGANISM: homo sapiens
<220> FEATURE:
<223> OTHER INFORMATION: miRNA: hsa-miR-20a

<400> SEQUENCE: 20
uaaagugcuu auagugcagg uag                                        23

<210> SEQ ID NO 21
<211> LENGTH: 21
<212> TYPE: RNA
<213> ORGANISM: homo sapiens
<220> FEATURE:
<223> OTHER INFORMATION: miRNA: hsa-miR-31

<400> SEQUENCE: 21
aggcaagaug cuggcauagc u                                          21

<210> SEQ ID NO 22
<211> LENGTH: 22
<212> TYPE: RNA
<213> ORGANISM: homo sapiens
<220> FEATURE:
<223> OTHER INFORMATION: miRNA: hsa-miR-187

<400> SEQUENCE: 22
ucgugucuug uguugcagcc gg                                         22

<210> SEQ ID NO 23
<211> LENGTH: 23
<212> TYPE: RNA
<213> ORGANISM: homo sapiens
<220> FEATURE:
<223> OTHER INFORMATION: miRNA: hsa-miR-301b

<400> SEQUENCE: 23
cagugcaaug auauugucaa agc                                        23
```

```
<210> SEQ ID NO 24
<211> LENGTH: 23
<212> TYPE: RNA
<213> ORGANISM: homo sapiens
<220> FEATURE:
<223> OTHER INFORMATION: miRNA: hsa-miR-142-3p

<400> SEQUENCE: 24
uguaguguuu ccuacuuuau gga                                                 23

<210> SEQ ID NO 25
<211> LENGTH: 23
<212> TYPE: RNA
<213> ORGANISM: homo sapiens
<220> FEATURE:
<223> OTHER INFORMATION: miRNA: hsa-miR-18a

<400> SEQUENCE: 25
uaaggugcau cuagugcaga uag                                                 23

<210> SEQ ID NO 26
<211> LENGTH: 23
<212> TYPE: RNA
<213> ORGANISM: homo sapiens
<220> FEATURE:
<223> OTHER INFORMATION: miRNA: hsa-miR-137

<400> SEQUENCE: 26
uuauugcuua agaauacgcg uag                                                 23

<210> SEQ ID NO 27
<211> LENGTH: 23
<212> TYPE: RNA
<213> ORGANISM: homo sapiens
<220> FEATURE:
<223> OTHER INFORMATION: miRNA: hsa-miR-9

<400> SEQUENCE: 27
ucuuugguua ucuagcugua uga                                                 23

<210> SEQ ID NO 28
<211> LENGTH: 22
<212> TYPE: RNA
<213> ORGANISM: homo sapiens
<220> FEATURE:
<223> OTHER INFORMATION: miRNA: hsa-miR-135b*

<400> SEQUENCE: 28
auguagggcu aaaagccaug gg                                                  22

<210> SEQ ID NO 29
<211> LENGTH: 22
<212> TYPE: RNA
<213> ORGANISM: homo sapiens
<220> FEATURE:
<223> OTHER INFORMATION: miRNA: hsa-miR-934

<400> SEQUENCE: 29
ugucuacuac uggagacacu gg                                                  22

<210> SEQ ID NO 30
<211> LENGTH: 22
<212> TYPE: RNA
<213> ORGANISM: homo sapiens
<220> FEATURE:
```

<223> OTHER INFORMATION: miRNA: hsa-miR-143*

<400> SEQUENCE: 30
ggugcagugc ugcaucucug gu    22

<210> SEQ ID NO 31
<211> LENGTH: 23
<212> TYPE: RNA
<213> ORGANISM: homo sapiens
<220> FEATURE:
<223> OTHER INFORMATION: miRNA: hsa-miR-361-3p

<400> SEQUENCE: 31 uccccaggu gugauucuga uuu    23

<210> SEQ ID NO 32
<211> LENGTH: 22
<212> TYPE: RNA
<213> ORGANISM: homo sapiens
<220> FEATURE:
<223> OTHER INFORMATION: miRNA: hsa-miR-129-3p

<400> SEQUENCE: 32
aagcccuuac cccaaaaagc au    22

<210> SEQ ID NO 33
<211> LENGTH: 22
<212> TYPE: RNA
<213> ORGANISM: homo sapiens
<220> FEATURE:
<223> OTHER INFORMATION: miRNA: hsa-miR-561

<400> SEQUENCE: 33
caaaguuuaa gauccuugaa gu    22

<210> SEQ ID NO 34
<211> LENGTH: 22
<212> TYPE: RNA
<213> ORGANISM: homo sapiens
<220> FEATURE:
<223> OTHER INFORMATION: miRNA: hsa-miR-548b-5p

<400> SEQUENCE: 34
aaaaguaauu gugguuuugg cc    22

<210> SEQ ID NO 35
<211> LENGTH: 22
<212> TYPE: RNA
<213> ORGANISM: homo sapiens
<220> FEATURE:
<223> OTHER INFORMATION: miRNA: hsa-miR-627

<400> SEQUENCE: 35
gugagucucu aagaaaagag ga    22

<210> SEQ ID NO 36
<211> LENGTH: 23
<212> TYPE: RNA
<213> ORGANISM: homo sapiens
<220> FEATURE:
<223> OTHER INFORMATION: miRNA: hsa-miR-92a-1*

<400> SEQUENCE: 36
agguugggau cgguugcaau gcu    23

```
<210> SEQ ID NO 37
<211> LENGTH: 22
<212> TYPE: RNA
<213> ORGANISM: homo sapiens
<220> FEATURE:
<223> OTHER INFORMATION: miRNA: hsa-miR-93*

<400> SEQUENCE: 37
acugcugagc uagcacuucc cg                                              22

<210> SEQ ID NO 38
<211> LENGTH: 21
<212> TYPE: RNA
<213> ORGANISM: homo sapiens
<220> FEATURE:
<223> OTHER INFORMATION: miRNA: hsa-miR-571

<400> SEQUENCE: 38
ugaguuggcc aucugaguga g                                               21

<210> SEQ ID NO 39
<211> LENGTH: 22
<212> TYPE: RNA
<213> ORGANISM: homo sapiens
<220> FEATURE:
<223> OTHER INFORMATION: miRNA: hsa-miR-7-1*

<400> SEQUENCE: 39
caacaaauca cagucugcca ua                                              22

<210> SEQ ID NO 40
<211> LENGTH: 22
<212> TYPE: RNA
<213> ORGANISM: homo sapiens
<220> FEATURE:
<223> OTHER INFORMATION: miRNA: hsa-miR-26a-2*

<400> SEQUENCE: 40
ccuauucuug auuacuuguu uc                                              22

<210> SEQ ID NO 41
<211> LENGTH: 22
<212> TYPE: RNA
<213> ORGANISM: homo sapiens
<220> FEATURE:
<223> OTHER INFORMATION: miRNA: hsa-miR-449b

<400> SEQUENCE: 41
aggcagugua uuguuagcug gc                                              22

<210> SEQ ID NO 42
<211> LENGTH: 22
<212> TYPE: RNA
<213> ORGANISM: homo sapiens
<220> FEATURE:
<223> OTHER INFORMATION: miRNA: hsa-miR-449a

<400> SEQUENCE: 42
uggcagugua uuguuagcug gu                                              22

<210> SEQ ID NO 43
<211> LENGTH: 22
<212> TYPE: RNA
<213> ORGANISM: homo sapiens
<220> FEATURE:
<223> OTHER INFORMATION: miRNA: hsa-miR-195*
```

```
<400> SEQUENCE: 43
ccaauauugg cugugcugcu cc                                             22

<210> SEQ ID NO 44
<211> LENGTH: 23
<212> TYPE: RNA
<213> ORGANISM: homo sapiens
<220> FEATURE:
<223> OTHER INFORMATION: miRNA: hsa-miR-567

<400> SEQUENCE: 44
aguauguucu uccaggacag aac                                            23

<210> SEQ ID NO 45
<211> LENGTH: 22
<212> TYPE: RNA
<213> ORGANISM: homo sapiens
<220> FEATURE:
<223> OTHER INFORMATION: miRNA: hsa-miR-29c*

<400> SEQUENCE: 45
ugaccgauuu cuccuggugu uc                                             22

<210> SEQ ID NO 46
<211> LENGTH: 22
<212> TYPE: RNA
<213> ORGANISM: homo sapiens
<220> FEATURE:
<223> OTHER INFORMATION: miRNA: hsa-miR-30e*

<400> SEQUENCE: 46
cuuucagucg gauguuuaca gc                                             22

<210> SEQ ID NO 47
<211> LENGTH: 22
<212> TYPE: RNA
<213> ORGANISM: homo sapiens
<220> FEATURE:
<223> OTHER INFORMATION: miRNA: hsa-miR-30a*

<400> SEQUENCE: 47
cuuucagucg gauguuugca gc                                             22

<210> SEQ ID NO 48
<211> LENGTH: 22
<212> TYPE: RNA
<213> ORGANISM: homo sapiens
<220> FEATURE:
<223> OTHER INFORMATION: miRNA: hsa-miR-29b-2*

<400> SEQUENCE: 48
cugguuucac augguggcuu ag                                             22

<210> SEQ ID NO 49
<211> LENGTH: 23
<212> TYPE: RNA
<213> ORGANISM: homo sapiens
<220> FEATURE:
<223> OTHER INFORMATION: miRNA: hsa-miR-135b

<400> SEQUENCE: 49
uauggcuuuu cauuccuaug uga                                            23

<210> SEQ ID NO 50
<211> LENGTH: 23
```

```
<212> TYPE: RNA
<213> ORGANISM: homo sapiens
<220> FEATURE:
<223> OTHER INFORMATION: miRNA: hsa-miR-767-5p

<400> SEQUENCE: 50
ugcaccaugg uugucugagc aug                                          23

<210> SEQ ID NO 51
<211> LENGTH: 22
<212> TYPE: RNA
<213> ORGANISM: homo sapiens
<220> FEATURE:
<223> OTHER INFORMATION: miRNA: hsa-miR-874

<400> SEQUENCE: 51
cugcccuggc ccgagggacc ga                                           22

<210> SEQ ID NO 52
<211> LENGTH: 22
<212> TYPE: RNA
<213> ORGANISM: homo sapiens
<220> FEATURE:
<223> OTHER INFORMATION: miRNA: hsa-miR-487a

<400> SEQUENCE: 52
aaucauacag ggacauccag uu                                           22

<210> SEQ ID NO 53
<211> LENGTH: 22
<212> TYPE: RNA
<213> ORGANISM: homo sapiens
<220> FEATURE:
<223> OTHER INFORMATION: miRNA: hsa-miR-655

<400> SEQUENCE: 53
auaauacaug guuaaccucu uu                                           22

<210> SEQ ID NO 54
<211> LENGTH: 22
<212> TYPE: RNA
<213> ORGANISM: homo sapiens
<220> FEATURE:
<223> OTHER INFORMATION: miRNA: hsa-miR-30d*

<400> SEQUENCE: 54
cuuucaguca gauguuugcu gc                                           22

<210> SEQ ID NO 55
<211> LENGTH: 23
<212> TYPE: RNA
<213> ORGANISM: homo sapiens
<220> FEATURE:
<223> OTHER INFORMATION: miRNA: hsa-miR-136

<400> SEQUENCE: 55
acuccauuug uuuugaugau gga                                          23

<210> SEQ ID NO 56
<211> LENGTH: 21
<212> TYPE: RNA
<213> ORGANISM: homo sapiens
<220> FEATURE:
<223> OTHER INFORMATION: miRNA: hsa-miR-509-5p

<400> SEQUENCE: 56
```

```
uacugcagac aguggcaauc a                                                    21

<210> SEQ ID NO 57
<211> LENGTH: 22
<212> TYPE: RNA
<213> ORGANISM: homo sapiens
<220> FEATURE:
<223> OTHER INFORMATION: miRNA: hsa-miR-365

<400> SEQUENCE: 57
uaaugccccu aaaaauccuu au                                                   22

<210> SEQ ID NO 58
<211> LENGTH: 22
<212> TYPE: RNA
<213> ORGANISM: homo sapiens
<220> FEATURE:
<223> OTHER INFORMATION: miRNA: hsa-miR-92a

<400> SEQUENCE: 58
uauugcacuu gucccggccu gu                                                   22

<210> SEQ ID NO 59
<211> LENGTH: 22
<212> TYPE: RNA
<213> ORGANISM: homo sapiens
<220> FEATURE:
<223> OTHER INFORMATION: miRNA: hsa-miR-130a

<400> SEQUENCE: 59
cagugcaaug uuaaagggc au                                                    22

<210> SEQ ID NO 60
<211> LENGTH: 22
<212> TYPE: RNA
<213> ORGANISM: homo sapiens
<220> FEATURE:
<223> OTHER INFORMATION: miRNA: hsa-miR-532-3p

<400> SEQUENCE: 60
caugccuuga guguaggacc gu                                                   22

<210> SEQ ID NO 61
<211> LENGTH: 22
<212> TYPE: RNA
<213> ORGANISM: homo sapiens
<220> FEATURE:
<223> OTHER INFORMATION: miRNA: hsa-miR-30b

<400> SEQUENCE: 61
uguaaacauc cuacacucag cu                                                   22

<210> SEQ ID NO 62
<211> LENGTH: 22
<212> TYPE: RNA
<213> ORGANISM: homo sapiens
<220> FEATURE:
<223> OTHER INFORMATION: miRNA: hsa-miR-140-5p

<400> SEQUENCE: 62
cagugguuuu acccuauggu ag                                                   22

<210> SEQ ID NO 63
<211> LENGTH: 24
<212> TYPE: RNA
<213> ORGANISM: homo sapiens
```

```
<220> FEATURE:
<223> OTHER INFORMATION: miRNA: hsa-miR-362-5p

<400> SEQUENCE: 63
aauccuugga accuaggugu gagu                                            24

<210> SEQ ID NO 64
<211> LENGTH: 23
<212> TYPE: RNA
<213> ORGANISM: homo sapiens
<220> FEATURE:
<223> OTHER INFORMATION: miRNA: hsa-miR-221

<400> SEQUENCE: 64
agcuacauug ucugcugggu uuc                                             23

<210> SEQ ID NO 65
<211> LENGTH: 22
<212> TYPE: RNA
<213> ORGANISM: homo sapiens
<220> FEATURE:
<223> OTHER INFORMATION: miRNA: hsa-let-7e

<400> SEQUENCE: 65
ugagguagga gguuguauag uu                                              22

<210> SEQ ID NO 66
<211> LENGTH: 23
<212> TYPE: RNA
<213> ORGANISM: homo sapiens
<220> FEATURE:
<223> OTHER INFORMATION: miRNA: hsa-miR-324-5p

<400> SEQUENCE: 66
cgcauccccu agggcauugg ugu                                             23

<210> SEQ ID NO 67
<211> LENGTH: 22
<212> TYPE: RNA
<213> ORGANISM: homo sapiens
<220> FEATURE:
<223> OTHER INFORMATION: miRNA: hsa-let-7a

<400> SEQUENCE: 67
ugagguagua gguuguauag uu                                              22

<210> SEQ ID NO 68
<211> LENGTH: 22
<212> TYPE: RNA
<213> ORGANISM: homo sapiens
<220> FEATURE:
<223> OTHER INFORMATION: miRNA: hsa-let-7d

<400> SEQUENCE: 68
agagguagua gguugcauag uu                                              22

<210> SEQ ID NO 69
<211> LENGTH: 22
<212> TYPE: RNA
<213> ORGANISM: homo sapiens
<220> FEATURE:
<223> OTHER INFORMATION: miRNA: hsa-miR-25

<400> SEQUENCE: 69
cauugcacuu gucucggucu ga                                              22
```

```
<210> SEQ ID NO 70
<211> LENGTH: 23
<212> TYPE: RNA
<213> ORGANISM: homo sapiens
<220> FEATURE:
<223> OTHER INFORMATION: miRNA: hsa-miR-20b

<400> SEQUENCE: 70
caaagugcuc auagugcagg uag                                              23

<210> SEQ ID NO 71
<211> LENGTH: 22
<212> TYPE: RNA
<213> ORGANISM: homo sapiens
<220> FEATURE:
<223> OTHER INFORMATION: miRNA: hsa-miR-491-5p

<400> SEQUENCE: 71 agugggaac ccuuccauga gg                                                22

<210> SEQ ID NO 72
<211> LENGTH: 22
<212> TYPE: RNA
<213> ORGANISM: homo sapiens
<220> FEATURE:
<223> OTHER INFORMATION: miRNA: hsa-miR-99b

<400> SEQUENCE: 72
cacccguaga accgaccuug cg                                               22

<210> SEQ ID NO 73
<211> LENGTH: 22
<212> TYPE: RNA
<213> ORGANISM: homo sapiens
<220> FEATURE:
<223> OTHER INFORMATION: miRNA: hsa-miR-345

<400> SEQUENCE: 73
gcugacuccu aguccagggc uc                                               22

<210> SEQ ID NO 74
<211> LENGTH: 24
<212> TYPE: RNA
<213> ORGANISM: homo sapiens
<220> FEATURE:
<223> OTHER INFORMATION: miRNA: hsa-miR-661

<400> SEQUENCE: 74
ugccugdguc ucuggccugc gcgu                                             24

<210> SEQ ID NO 75
<211> LENGTH: 22
<212> TYPE: RNA
<213> ORGANISM: homo sapiens
<220> FEATURE:
<223> OTHER INFORMATION: miRNA: hsa-miR-376a*

<400> SEQUENCE: 75
guagauucuc cuucuaugag ua                                               22

<210> SEQ ID NO 76
<211> LENGTH: 22
<212> TYPE: RNA
<213> ORGANISM: homo sapiens
<220> FEATURE:
<223> OTHER INFORMATION: miRNA: hsa-miR-625*
```

```
<400> SEQUENCE: 76
gacuauagaa cuuuccccu ca                                                    22

<210> SEQ ID NO 77
<211> LENGTH: 22
<212> TYPE: RNA
<213> ORGANISM: homo sapiens
<220> FEATURE:
<223> OTHER INFORMATION: miRNA: hsa-miR-766

<400> SEQUENCE: 77
acuccagccc cacagccuca gc                                                   22

<210> SEQ ID NO 78
<211> LENGTH: 23
<212> TYPE: RNA
<213> ORGANISM: homo sapiens
<220> FEATURE:
<223> OTHER INFORMATION: miRNA: hsa-miR-200c

<400> SEQUENCE: 78
uaauacugcc ggguaaugau gga                                                  23

<210> SEQ ID NO 79
<211> LENGTH: 22
<212> TYPE: RNA
<213> ORGANISM: homo sapiens
<220> FEATURE:
<223> OTHER INFORMATION: miRNA: hsa-miR-598

<400> SEQUENCE: 79
uacgucaucg uugucaucgu ca                                                   22

<210> SEQ ID NO 80
<211> LENGTH: 23
<212> TYPE: RNA
<213> ORGANISM: homo sapiens
<220> FEATURE:
<223> OTHER INFORMATION: miRNA: hsa-miR-135a

<400> SEQUENCE: 80
uauggcuuuu uauuccuaug uga                                                  23

<210> SEQ ID NO 81
<211> LENGTH: 22
<212> TYPE: RNA
<213> ORGANISM: homo sapiens
<220> FEATURE:
<223> OTHER INFORMATION: miRNA: hsa-miR-184

<400> SEQUENCE: 81
uggacggaga acugauaagg gu                                                   22

<210> SEQ ID NO 82
<211> LENGTH: 22
<212> TYPE: RNA
<213> ORGANISM: homo sapiens
<220> FEATURE:
<223> OTHER INFORMATION: miRNA: hsa-miR-654-5p

<400> SEQUENCE: 82
uggugggccg cagaacaugu gc                                                   22

<210> SEQ ID NO 83
```

<211> LENGTH: 22
<212> TYPE: RNA
<213> ORGANISM: homo sapiens
<220> FEATURE:
<223> OTHER INFORMATION: miRNA: hsa-miR-154

<400> SEQUENCE: 83
uagguuaucc guguugccuu cg                                                  22

<210> SEQ ID NO 84
<211> LENGTH: 21
<212> TYPE: RNA
<213> ORGANISM: homo sapiens
<220> FEATURE:
<223> OTHER INFORMATION: miRNA: hsa-miR-499-5p

<400> SEQUENCE: 84
uuaagacuug cagugauguu u                                                   21

<210> SEQ ID NO 85
<211> LENGTH: 22
<212> TYPE: RNA
<213> ORGANISM: homo sapiens
<220> FEATURE:
<223> OTHER INFORMATION: miRNA: hsa-miR-299-5p

<400> SEQUENCE: 85
ugguuuaccg ucccacauac au                                                  22

<210> SEQ ID NO 86
<211> LENGTH: 21
<212> TYPE: RNA
<213> ORGANISM: homo sapiens
<220> FEATURE:
<223> OTHER INFORMATION: miRNA: hsa-miR-431

<400> SEQUENCE: 86
ugucuugcag gccgucaugc a                                                   21

<210> SEQ ID NO 87
<211> LENGTH: 22
<212> TYPE: RNA
<213> ORGANISM: homo sapiens
<220> FEATURE:
<223> OTHER INFORMATION: miRNA: hsa-miR-381

<400> SEQUENCE: 87
uauacaaggg caagcucucu gu                                                  22

<210> SEQ ID NO 88
<211> LENGTH: 21
<212> TYPE: RNA
<213> ORGANISM: homo sapiens
<220> FEATURE:
<223> OTHER INFORMATION: miRNA: hsa-miR-337-5p

<400> SEQUENCE: 88
gaacggcuuc auacaggagu u                                                   21

<210> SEQ ID NO 89
<211> LENGTH: 22
<212> TYPE: RNA
<213> ORGANISM: homo sapiens
<220> FEATURE:
<223> OTHER INFORMATION: miRNA: hsa-miR-369-5p

<400> SEQUENCE: 89

```
agaucgaccg uguuauauuc gc                                              22

<210> SEQ ID NO 90
<211> LENGTH: 22
<212> TYPE: RNA
<213> ORGANISM: homo sapiens
<220> FEATURE:
<223> OTHER INFORMATION: miRNA: hsa-miR-154*

<400> SEQUENCE: 90
aaucauacac gguugaccua uu                                              22

<210> SEQ ID NO 91
<211> LENGTH: 22
<212> TYPE: RNA
<213> ORGANISM: homo sapiens
<220> FEATURE:
<223> OTHER INFORMATION: miRNA: hsa-miR-615-5p

<400> SEQUENCE: 91
gggggucccc ggugcucgga uc                                              22

<210> SEQ ID NO 92
<211> LENGTH: 23
<212> TYPE: RNA
<213> ORGANISM: homo sapiens
<220> FEATURE:
<223> OTHER INFORMATION: miRNA: hsa-miR-542-5p

<400> SEQUENCE: 92
ucggggauca ucaugucacg aga                                             23

<210> SEQ ID NO 93
<211> LENGTH: 22
<212> TYPE: RNA
<213> ORGANISM: homo sapiens
<220> FEATURE:
<223> OTHER INFORMATION: miRNA: hsa-miR-539

<400> SEQUENCE: 93
ggagaaauua uccuuggugu gu                                              22

<210> SEQ ID NO 94
<211> LENGTH: 21
<212> TYPE: RNA
<213> ORGANISM: homo sapiens
<220> FEATURE:
<223> OTHER INFORMATION: miRNA: hsa-miR-379

<400> SEQUENCE: 94
ugguagacua uggaacguag g                                               21

<210> SEQ ID NO 95
<211> LENGTH: 21
<212> TYPE: RNA
<213> ORGANISM: homo sapiens
<220> FEATURE:
<223> OTHER INFORMATION: miRNA: hsa-miR-376a

<400> SEQUENCE: 95
aucauagagg aaaauccacg u                                               21

<210> SEQ ID NO 96
<211> LENGTH: 22
<212> TYPE: RNA
```

```
<213> ORGANISM: homo sapiens
<220> FEATURE:
<223> OTHER INFORMATION: miRNA: hsa-miR-19a*

<400> SEQUENCE: 96
aguuuugcau aguugcacua ca                                    22

<210> SEQ ID NO 97
<211> LENGTH: 22
<212> TYPE: RNA
<213> ORGANISM: homo sapiens
<220> FEATURE:
<223> OTHER INFORMATION: miRNA: hsa-miR-586

<400> SEQUENCE: 97
uaugcauugu auuuuuaggu cc                                    22

<210> SEQ ID NO 98
<211> LENGTH: 20
<212> TYPE: RNA
<213> ORGANISM: homo sapiens
<220> FEATURE:
<223> OTHER INFORMATION: miRNA: hsa-miR-760

<400> SEQUENCE: 98
cggcucuggg ucugugggga                                       20

<210> SEQ ID NO 99
<211> LENGTH: 22
<212> TYPE: RNA
<213> ORGANISM: homo sapiens
<220> FEATURE:
<223> OTHER INFORMATION: miRNA: hsa-let-7e*

<400> SEQUENCE: 99
cuauacggcc uccuagcuuu cc                                    22

<210> SEQ ID NO 100
<211> LENGTH: 22
<212> TYPE: RNA
<213> ORGANISM: homo sapiens
<220> FEATURE:
<223> OTHER INFORMATION: miRNA: hsa-miR-30d

<400> SEQUENCE: 100
uguaaacauc cccgacugga ag                                    22

<210> SEQ ID NO 101
<211> LENGTH: 22
<212> TYPE: RNA
<213> ORGANISM: homo sapiens
<220> FEATURE:
<223> OTHER INFORMATION: miRNA: hsa-miR-27a*

<400> SEQUENCE: 101
agggcuuagc ugcuugugag ca                                    22

<210> SEQ ID NO 102
<211> LENGTH: 23
<212> TYPE: RNA
<213> ORGANISM: homo sapiens
<220> FEATURE:
<223> OTHER INFORMATION: miRNA: hsa-miR-941

<400> SEQUENCE: 102
cacccggcug ugugcacaug ugc                                   23
```

```
<210> SEQ ID NO 103
<211> LENGTH: 22
<212> TYPE: RNA
<213> ORGANISM: homo sapiens
<220> FEATURE:
<223> OTHER INFORMATION: miRNA: hsa-miR-493*

<400> SEQUENCE: 103
uuguacaugg uaggcuuuca uu                                          22

<210> SEQ ID NO 104
<211> LENGTH: 22
<212> TYPE: RNA
<213> ORGANISM: homo sapiens
<220> FEATURE:
<223> OTHER INFORMATION: miRNA: hsa-miR-584

<400> SEQUENCE: 104
uuaugguuug ccugggacug ag                                          22

<210> SEQ ID NO 105
<211> LENGTH: 22
<212> TYPE: RNA
<213> ORGANISM: homo sapiens
<220> FEATURE:
<223> OTHER INFORMATION: miRNA: hsa-miR-193b*

<400> SEQUENCE: 105
cgggguuuug agggcgagau ga                                          22

<210> SEQ ID NO 106
<211> LENGTH: 22
<212> TYPE: RNA
<213> ORGANISM: homo sapiens
<220> FEATURE:
<223> OTHER INFORMATION: miRNA: hsa-miR-200c*

<400> SEQUENCE: 106
cgucuuaccc agcaguguuu gg                                          22

<210> SEQ ID NO 107
<211> LENGTH: 22
<212> TYPE: RNA
<213> ORGANISM: homo sapiens
<220> FEATURE:
<223> OTHER INFORMATION: miRNA: hsa-miR-147b

<400> SEQUENCE: 107
gugugcggaa augcuucugc ua                                          22
```